US008827979B2

(12) United States Patent
Pesach et al.

(10) Patent No.: US 8,827,979 B2
(45) Date of Patent: Sep. 9, 2014

(54) DRUG DELIVERY DEVICE

(75) Inventors: Benny Pesach, Rosh-ha ayin (IL);
Gabriel Bitton, Jerusalem (IL); Ram Weiss, Haifa (IL); Ron Nagar, Tel Aviv (IL)

(73) Assignee: Insuline Medical Ltd., Petach-Tikva (IL)

( * ) Notice: Subject to any disclaimer, the term of this patent is extended or adjusted under 35 U.S.C. 154(b) by 917 days.

(21) Appl. No.: 12/450,251

(22) PCT Filed: Mar. 19, 2008

(86) PCT No.: PCT/IB2008/051049
§ 371 (c)(1),
(2), (4) Date: Jan. 15, 2010

(87) PCT Pub. No.: WO2008/114223
PCT Pub. Date: Sep. 25, 2008

(65) Prior Publication Data
US 2010/0174225 A1      Jul. 8, 2010

Related U.S. Application Data

(63) Continuation-in-part of application No. 11/821,230, filed on Jun. 21, 2007.

(60) Provisional application No. 61/010,758, filed on Jan. 10, 2008, provisional application No. 61/016,571, filed on Dec. 25, 2007, provisional application No. 61/008,277, filed on Dec. 18, 2007, provisional application No. 60/940,721, filed on May 30, 2007, provisional application No. 60/912,698, filed on Apr. 19, 2007, provisional application No. 60/895,519, filed on Mar. 19, 2007, provisional application No. 60/895,518, filed on Mar. 19, 2007.

(51) Int. Cl.
*A61M 31/00*      (2006.01)
*A61F 7/12*      (2006.01)
*A61B 18/14*      (2006.01)
*A61N 1/30*      (2006.01)

(52) U.S. Cl.
USPC ............. 604/500; 604/113; 604/114; 604/20; 604/21

(58) Field of Classification Search
USPC ............... 604/112–114, 500, 501, 20, 22, 83, 604/191, 21, 181, 187, 218, 66, 68–70, 506, 604/131, 290
See application file for complete search history.

(56) References Cited

U.S. PATENT DOCUMENTS 3,620,209 A   11/1971  Kravitz
3,683,911 A    8/1972  McCormick
(Continued)

FOREIGN PATENT DOCUMENTS

EP   1611848   1/2006
EP   1695664   8/2006
(Continued)

OTHER PUBLICATIONS

Belinda et. al., (1996), Journal of Physiology, 572.3:811-820.
(Continued)

*Primary Examiner* — Bhisma Mehta
*Assistant Examiner* — Bradley G Thomas, Jr.
(74) *Attorney, Agent, or Firm* — Cooley LLP; Brian P. Hopkins

(57) ABSTRACT

The present disclosure presents systems, devices and methods for injection of drugs, substances and/or chemicals to a patient and for improving their effectiveness once they are injected are disclosed. Additional treatment can be applied to a tissue region on the patient into which a drug (e.g., insulin) is injected, to expose the tissue region to various forms of energy or a substance to improve the drug's pharmacokinetic and/or pharmacodynamic profile.

46 Claims, 15 Drawing Sheets

(56) References Cited

U.S. PATENT DOCUMENTS

| | | | |
|---|---|---|---|
| 4,230,105 A | 10/1980 | Harwood | |
| H71 H | 5/1986 | Sorenson et al. | |
| 4,628,928 A | 12/1986 | Lowell | |
| 4,685,911 A | 8/1987 | Konno et al. | |
| 4,744,787 A | 5/1988 | Phipps et al. | |
| 4,747,819 A | 5/1988 | Phipps et al. | |
| 4,771,772 A | 9/1988 | DeWitt | |
| 4,898,592 A | 2/1990 | Latzke et al. | |
| 4,948,587 A | 8/1990 | Kost et al. | |
| 4,963,360 A | 10/1990 | Argaud | |
| 4,987,897 A | 1/1991 | Funke | |
| 4,998,930 A | 3/1991 | Lundahl | |
| 5,047,007 A | 9/1991 | McNichols et al. | |
| 5,053,033 A | 10/1991 | Clarke | |
| 5,098,429 A | 3/1992 | Sterzer | |
| 5,113,859 A | 5/1992 | Funke | |
| 5,135,477 A | 8/1992 | Untereker et al. | |
| 5,213,568 A | 5/1993 | Lattin et al. | |
| 5,243,986 A | 9/1993 | Wurster | |
| 5,271,736 A | 12/1993 | Picha | |
| 5,306,252 A | 4/1994 | Yutori et al. | |
| 5,307,816 A | 5/1994 | Hashimoto et al. | |
| 5,324,521 A | 6/1994 | Gertner et al. | |
| 5,332,577 A | 7/1994 | Gertner et al. | |
| 5,354,324 A | 10/1994 | Gregory | |
| 5,378,475 A | 1/1995 | Smith et al. | |
| 5,383,873 A | 1/1995 | Hoey et al. | |
| 5,411,550 A | 5/1995 | Herweck et al. | |
| 5,430,016 A * | 7/1995 | Balschmidt et al. | 514/5.9 |
| 5,498,254 A | 3/1996 | Hoey et al. | |
| 5,512,048 A | 4/1996 | Slettenmark | |
| 5,523,092 A | 6/1996 | Hanson et al. | |
| 5,525,356 A | 6/1996 | Jevne et al. | |
| 5,527,292 A | 6/1996 | Adams et al. | |
| 5,545,208 A | 8/1996 | Wolff et al. | |
| 5,556,421 A | 9/1996 | Prutchi et al. | |
| 5,564,439 A | 10/1996 | Picha | |
| 5,567,592 A | 10/1996 | Benet et al. | |
| 5,571,152 A | 11/1996 | Chen et al. | |
| 5,590,657 A | 1/1997 | Cain et al. | |
| 5,591,445 A | 1/1997 | Hoey et al. | |
| 5,634,468 A | 6/1997 | Platt et al. | |
| 5,658,583 A | 8/1997 | Zhang et al. | |
| 5,706,807 A | 1/1998 | Picha | |
| 5,713,847 A | 2/1998 | Howard, III et al. | |
| 5,725,017 A | 3/1998 | Elsberry et al. | |
| 5,725,567 A | 3/1998 | Wolff et al. | |
| 5,730,125 A | 3/1998 | Prutchi et al. | |
| 5,741,211 A | 4/1998 | Renirie et al. | |
| 5,798,065 A | 8/1998 | Picha | |
| 5,843,051 A | 12/1998 | Adams et al. | |
| 5,851,217 A | 12/1998 | Wolff et al. | |
| 5,851,231 A | 12/1998 | Wolff et al. | |
| 5,871,446 A | 2/1999 | Wilk | |
| 5,871,535 A | 2/1999 | Wolff et al. | |
| 5,882,332 A | 3/1999 | Wijay | |
| 5,919,216 A | 7/1999 | Houben et al. | |
| 5,919,479 A | 7/1999 | Zhang et al. | |
| 5,997,468 A | 12/1999 | Wolff et al. | |
| 6,004,346 A | 12/1999 | Wolff et al. | |
| 6,004,927 A | 12/1999 | Benet et al. | |
| 6,026,316 A | 2/2000 | Kucharczyk et al. | |
| 6,028,054 A | 2/2000 | Benet et al. | |
| 6,043,273 A | 3/2000 | Duhaylongsod | |
| 6,060,454 A | 5/2000 | Duhaylongsod | |
| 6,061,587 A | 5/2000 | Kucharczyk et al. | |
| 6,087,394 A | 7/2000 | Duhaylongsod | |
| 6,093,167 A | 7/2000 | Houben et al. | |
| 6,101,412 A | 8/2000 | Duhaylongsod | |
| 6,122,536 A | 9/2000 | Sun et al. | |
| 6,125,290 A | 9/2000 | Miesel | |
| 6,125,291 A | 9/2000 | Miesel et al. | |
| 6,127,117 A | 10/2000 | Morris et al. | |
| 6,127,410 A | 10/2000 | Duhaylongsod | |
| 6,133,242 A | 10/2000 | Zalewski et al. | |
| 6,134,459 A | 10/2000 | Roberts et al. | |
| 6,135,978 A | 10/2000 | Houben et al. | |
| 6,141,589 A | 10/2000 | Duhaylongsod | |
| 6,144,866 A | 11/2000 | Miesel et al. | |
| 6,152,898 A | 11/2000 | Olsen | |
| 6,156,029 A | 12/2000 | Mueller | |
| 6,161,047 A | 12/2000 | King et al. | |
| 6,198,952 B1 | 3/2001 | Miesel | |
| 6,198,966 B1 | 3/2001 | Heruth | |
| 6,210,368 B1 | 4/2001 | Rogers | |
| 6,228,050 B1 | 5/2001 | Olsen et al. | |
| 6,228,595 B1 | 5/2001 | Morris et al. | |
| 6,238,367 B1 | 5/2001 | Christiansen et al. | |
| 6,245,347 B1 | 6/2001 | Zhang et al. | |
| 6,247,812 B1 | 6/2001 | Miehle et al. | |
| 6,254,598 B1 | 7/2001 | Edwards et al. | |
| 6,261,280 B1 | 7/2001 | Houben et al. | |
| 6,261,595 B1 | 7/2001 | Stanley et al. | |
| 6,269,340 B1 | 7/2001 | Ford et al. | |
| 6,283,949 B1 | 9/2001 | Roorda | |
| 6,284,266 B1 | 9/2001 | Zhang et al. | |
| 6,292,702 B1 | 9/2001 | King et al. | |
| 6,296,630 B1 | 10/2001 | Altman et al. | |
| 6,303,142 B1 | 10/2001 | Zhang et al. | |
| 6,305,381 B1 | 10/2001 | Weijand et al. | |
| 6,306,431 B1 | 10/2001 | Zhang et al. | |
| 6,312,412 B1 * | 11/2001 | Saied et al. | 604/191 |
| 6,323,184 B1 | 11/2001 | Zalewski et al. | |
| 6,338,850 B1 | 1/2002 | Jevnikar et al. | |
| 6,340,472 B1 | 1/2002 | Zhang et al. | |
| 6,342,250 B1 | 1/2002 | Masters | |
| 6,350,276 B1 | 2/2002 | Knowlton | |
| 6,375,628 B1 | 4/2002 | Zadno-Azizi et al. | |
| 6,377,846 B1 | 4/2002 | Chornenky et al. | |
| 6,379,382 B1 | 4/2002 | Yang | |
| 6,385,491 B1 | 5/2002 | Lindemans et al. | |
| 6,389,313 B1 | 5/2002 | Marchitto et al. | |
| 6,395,015 B1 | 5/2002 | Borst et al. | |
| 6,414,018 B1 | 7/2002 | Duhaylongsod | |
| 6,416,510 B1 | 7/2002 | Altman et al. | |
| 6,425,853 B1 | 7/2002 | Edwards | |
| 6,427,088 B1 | 7/2002 | Bowman, IV et al. | |
| 6,442,435 B2 | 8/2002 | King et al. | |
| 6,447,443 B1 | 9/2002 | Keogh et al. | |
| 6,449,507 B1 | 9/2002 | Hill et al. | |
| 6,453,195 B1 | 9/2002 | Thompson | |
| 6,453,648 B1 | 9/2002 | Zhang et al. | |
| 6,456,883 B1 | 9/2002 | Torgerson et al. | |
| 6,458,102 B1 | 10/2002 | Mann et al. | |
| 6,458,118 B1 | 10/2002 | Lent et al. | |
| 6,461,329 B1 | 10/2002 | Van Antwerp et al. | |
| 6,465,006 B1 | 10/2002 | Zhang et al. | |
| 6,465,709 B1 | 10/2002 | Sun et al. | |
| 6,471,675 B1 | 10/2002 | Rogers et al. | |
| 6,471,689 B1 | 10/2002 | Joseph et al. | |
| 6,482,214 B1 | 11/2002 | Sidor, Jr. et al. | |
| 6,485,464 B1 | 11/2002 | Christenson et al. | |
| 6,487,446 B1 | 11/2002 | Hill et al. | |
| 6,488,959 B2 | 12/2002 | Stanley et al. | |
| 6,511,428 B1 | 1/2003 | Azuma et al. | |
| 6,512,958 B1 | 1/2003 | Swoyer et al. | |
| 6,528,086 B2 | 3/2003 | Zhang | |
| 6,532,388 B1 | 3/2003 | Hill et al. | |
| 6,537,242 B1 * | 3/2003 | Palmer | 604/22 |
| 6,542,350 B1 | 4/2003 | Rogers | |
| 6,544,212 B2 | 4/2003 | Galley et al. | |
| 6,546,281 B1 | 4/2003 | Zhang et al. | |
| 6,551,276 B1 | 4/2003 | Mann et al. | |
| 6,551,346 B2 | 4/2003 | Crossley | |
| 6,554,798 B1 | 4/2003 | Mann et al. | |
| 6,558,345 B1 | 5/2003 | Houben et al. | |
| 6,558,382 B2 | 5/2003 | Jahns et al. | |
| 6,562,001 B2 | 5/2003 | Lebel et al. | |
| 6,564,105 B2 | 5/2003 | Starkweather et al. | |
| 6,571,125 B2 | 5/2003 | Thompson | |
| 6,572,542 B1 | 6/2003 | Houben et al. | |
| 6,572,583 B1 | 6/2003 | Olsen et al. | |
| 6,577,899 B2 | 6/2003 | Lebel et al. | |
| 6,584,335 B1 | 6/2003 | Haar et al. | |

(56) References Cited

U.S. PATENT DOCUMENTS

| | | |
|---|---|---|
| 6,584,360 B2 | 6/2003 | Francischelli et al. |
| 6,585,644 B2 | 7/2003 | Lebel et al. |
| 6,585,707 B2 | 7/2003 | Cabiri et al. |
| 6,592,519 B1 | 7/2003 | Martinez |
| 6,597,946 B2 | 7/2003 | Avrahami et al. |
| 6,605,039 B2 | 8/2003 | Houben et al. |
| 6,613,082 B2 | 9/2003 | Yang |
| 6,613,084 B2 | 9/2003 | Yang |
| 6,613,350 B1 | 9/2003 | Zhang et al. |
| 6,615,083 B2 | 9/2003 | Kupper |
| 6,620,151 B2 | 9/2003 | Blischak et al. |
| 6,622,731 B2 | 9/2003 | Daniel et al. |
| 6,626,867 B1 | 9/2003 | Christenson et al. |
| 6,628,987 B1 | 9/2003 | Hill et al. |
| 6,628,989 B1 | 9/2003 | Penner et al. |
| 6,635,167 B1 | 10/2003 | Batman et al. |
| 6,644,321 B1 | 11/2003 | Behm |
| 6,645,176 B1 | 11/2003 | Christenson et al. |
| 6,647,299 B2 | 11/2003 | Bourget |
| 6,648,821 B2 | 11/2003 | Lebel et al. |
| 6,650,935 B1 | 11/2003 | Watmough |
| 6,659,948 B2 | 12/2003 | Lebel et al. |
| 6,669,663 B1 | 12/2003 | Thompson |
| 6,673,070 B2 | 1/2004 | Davis et al. |
| 6,673,596 B1 | 1/2004 | Sayler et al. |
| 6,675,049 B2 | 1/2004 | Thompson et al. |
| 6,681,135 B1 | 1/2004 | Reinke et al. |
| 6,685,452 B2 | 2/2004 | Christiansen et al. |
| 6,687,546 B2 | 2/2004 | Lebel et al. |
| 6,690,973 B2 | 2/2004 | Hill et al. |
| 6,694,191 B2 | 2/2004 | Starkweather et al. |
| 6,697,667 B1 | 2/2004 | Lee et al. |
| 6,706,038 B2 | 3/2004 | Francischelli et al. |
| 6,711,436 B1 | 3/2004 | Duhaylongsod |
| 6,714,822 B2 | 3/2004 | King et al. |
| 6,716,178 B1 | 4/2004 | Kilpatrick et al. |
| 6,718,208 B2 | 4/2004 | Hill et al. |
| 6,723,087 B2 | 4/2004 | O'Neill et al. |
| 6,726,673 B1 | 4/2004 | Zhang et al. |
| 6,728,574 B2 | 4/2004 | Ujhelyi et al. |
| 6,733,446 B2 | 5/2004 | Lebel et al. |
| 6,733,474 B2 | 5/2004 | Kusleika |
| 6,733,476 B2 | 5/2004 | Christenson et al. |
| 6,733,500 B2 | 5/2004 | Kelley et al. |
| 6,735,471 B2 | 5/2004 | Hill et al. |
| 6,736,789 B1 | 5/2004 | Spickermann |
| 6,736,797 B1 | 5/2004 | Larsen et al. |
| 6,738,671 B2 | 5/2004 | Christophersom et al. |
| 6,740,075 B2 | 5/2004 | Lebel et al. |
| 6,743,204 B2 | 6/2004 | Christenson et al. |
| 6,743,227 B2 | 6/2004 | Seraj et al. |
| 6,744,350 B2 | 6/2004 | Blomquist |
| 6,748,653 B2 | 6/2004 | Lindemans et al. |
| 6,752,155 B2 | 6/2004 | Behm |
| 6,755,849 B1 | 6/2004 | Gowda et al. |
| 6,756,053 B2 | 6/2004 | Zhang et al. |
| 6,758,810 B2 | 7/2004 | Lebel et al. |
| 6,758,828 B2 | 7/2004 | Hammer et al. |
| 6,764,446 B2 | 7/2004 | Wolinsky et al. |
| 6,766,183 B2 | 7/2004 | Walsh et al. |
| 6,780,426 B2 | 8/2004 | Zhang et al. |
| 6,799,149 B2 | 9/2004 | Hartlaub |
| 6,804,558 B2 | 10/2004 | Haller et al. |
| 6,805,667 B2 | 10/2004 | Christopherson et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,823,213 B1 | 11/2004 | Norris et al. |
| 6,827,702 B2 | 12/2004 | Lebel et al. |
| 6,836,687 B2 | 12/2004 | Kelley et al. |
| 6,846,823 B2 | 1/2005 | Landau et al. |
| 6,852,104 B2 | 2/2005 | Blomquist |
| 6,852,694 B2 | 2/2005 | Van Antwerp et al. |
| 6,865,419 B2 | 3/2005 | Mulligan et al. |
| 6,866,678 B2 | 3/2005 | Shenderova et al. |
| 6,872,200 B2 | 3/2005 | Mann et al. |
| 6,873,268 B2 | 3/2005 | Lebel et al. |
| 6,878,529 B2 | 4/2005 | Harrow et al. |
| 6,887,238 B2 | 5/2005 | Jahns et al. |
| 6,904,318 B2 | 6/2005 | Hill et al. |
| 6,913,763 B2 | 7/2005 | Lerner |
| 6,915,157 B2 | 7/2005 | Bennett et al. |
| 6,922,585 B2 | 7/2005 | Zhou et al. |
| 6,923,784 B2 | 8/2005 | Stein |
| 6,925,393 B1 | 8/2005 | Kalatz et al. |
| 6,927,246 B2 | 8/2005 | Noronha et al. |
| 6,928,338 B1 | 8/2005 | Buchser et al. |
| 6,930,602 B2 | 8/2005 | Villaseca et al. |
| 6,936,029 B2 | 8/2005 | Mann et al. |
| 6,950,708 B2 | 9/2005 | Bowman, IV et al. |
| 6,955,661 B1 | 10/2005 | Herweck et al. |
| 6,955,819 B2 | 10/2005 | Zhang et al. |
| 6,958,705 B2 | 10/2005 | Lebel et al. |
| 6,961,448 B2 | 11/2005 | Nichols et al. |
| 6,962,584 B1 | 11/2005 | Stone et al. |
| 6,966,322 B2 | 11/2005 | McVenes et al. |
| 6,969,369 B2 | 11/2005 | Struble |
| 6,974,437 B2 | 12/2005 | Lebel et al. |
| 6,978,174 B2 | 12/2005 | Gelfand et al. |
| 6,979,315 B2 | 12/2005 | Rogers et al. |
| 6,979,326 B2 | 12/2005 | Mann et al. |
| 6,979,351 B2 | 12/2005 | Forsell et al. |
| 6,984,229 B2 | 1/2006 | Neuberger |
| 6,985,768 B2 | 1/2006 | Hemming et al. |
| 6,991,916 B2 | 1/2006 | Benson et al. |
| 6,997,920 B2 | 2/2006 | Mann et al. |
| 7,011,630 B2 | 3/2006 | Desai et al. |
| 7,013,177 B1 | 3/2006 | Whitehurst et al. |
| 7,018,384 B2 | 3/2006 | Skakoon |
| 7,018,568 B2 | 3/2006 | Tierney |
| 7,024,236 B2 | 4/2006 | Ford et al. |
| 7,024,245 B2 | 4/2006 | Lebel et al. |
| 7,024,248 B2 | 4/2006 | Penner et al. |
| 7,025,743 B2 | 4/2006 | Mann et al. |
| 7,025,760 B2 | 4/2006 | Miller et al. |
| 7,027,856 B2 | 4/2006 | Zhou et al. |
| 7,027,871 B2 | 4/2006 | Burnes et al. |
| 7,033,338 B2 | 4/2006 | Vilks et al. |
| 7,041,704 B2 | 5/2006 | Burgard et al. |
| 7,044,082 B1 | 5/2006 | Hewett et al. |
| 7,052,483 B2 | 5/2006 | Wojcik |
| 7,054,782 B2 | 5/2006 | Hartlaub |
| 7,058,447 B2 | 6/2006 | Hill et al. |
| 7,063,684 B2 | 6/2006 | Moberg |
| 7,066,891 B2 | 6/2006 | Stadler et al. |
| 7,066,909 B1 | 6/2006 | Peter et al. |
| 7,069,078 B2 | 6/2006 | Houben |
| 7,072,802 B2 | 7/2006 | Hartlaub |
| 7,074,233 B1 | 7/2006 | Gowda et al. |
| 7,084,116 B2 | 8/2006 | Fraser et al. |
| 7,092,753 B2 | 8/2006 | Darvish et al. |
| 7,094,228 B2 | 8/2006 | Zhang et al. |
| 7,101,857 B2 | 9/2006 | Sung et al. |
| 7,107,086 B2 | 9/2006 | Reihl et al. |
| 7,107,093 B2 | 9/2006 | Burnes |
| 7,108,696 B2 | 9/2006 | Daniel et al. |
| 7,109,878 B2 | 9/2006 | Mann et al. |
| 7,115,606 B2 | 10/2006 | Landau et al. |
| 7,123,968 B1 | 10/2006 | Casscells, III et al. |
| 7,125,407 B2 | 10/2006 | Edwards et al. |
| 7,125,848 B2 | 10/2006 | Fraser et al. |
| 7,133,329 B2 | 11/2006 | Skyggebjerg et al. |
| 7,149,581 B2 | 12/2006 | Goedeke |
| 7,149,773 B2 | 12/2006 | Haller et al. |
| 7,150,975 B2 | 12/2006 | Tamada et al. |
| 7,151,961 B2 | 12/2006 | Whitehurst et al. |
| 7,160,252 B2 | 1/2007 | Cho et al. |
| 7,162,303 B2 | 1/2007 | Levin et al. |
| 7,162,307 B2 | 1/2007 | Patrias |
| 7,163,511 B2 | 1/2007 | Conn et al. |
| 7,164,948 B2 | 1/2007 | Struble et al. |
| 7,167,743 B2 | 1/2007 | Heruth et al. |
| 7,171,263 B2 | 1/2007 | Darvish et al. |

(56) References Cited

U.S. PATENT DOCUMENTS

| | | |
|---|---|---|
| 7,171,274 B2 | 1/2007 | Starkweather et al. |
| 7,179,226 B2 | 2/2007 | Crothall et al. |
| 7,181,505 B2 | 2/2007 | Haller et al. |
| 7,184,828 B2 | 2/2007 | Hill et al. |
| 7,184,829 B2 | 2/2007 | Hill et al. |
| 7,186,247 B2 | 3/2007 | Ujhelyi et al. |
| 7,187,979 B2 | 3/2007 | Haubrich et al. |
| 7,190,997 B1 | 3/2007 | Darvish et al. |
| 7,191,008 B2 | 3/2007 | Schmidt et al. |
| 7,193,521 B2 | 3/2007 | Moberg et al. |
| 7,203,541 B2 | 4/2007 | Sowelam et al. |
| 7,206,632 B2 | 4/2007 | King |
| 7,209,784 B2 | 4/2007 | Schmidt |
| 7,209,790 B2 | 4/2007 | Thompson et al. |
| 7,218,964 B2 | 5/2007 | Hill et al. |
| 2001/0022279 A1 | 9/2001 | Denyer et al. |
| 2001/0047195 A1 | 11/2001 | Crossley |
| 2002/0026141 A1 | 2/2002 | Houben et al. |
| 2002/0032406 A1 | 3/2002 | Kusleika |
| 2002/1003810 | 3/2002 | Avrahami et al. |
| 2002/0040208 A1* | 4/2002 | Flaherty et al. .......... 604/288.01 |
| 2002/0068869 A1 | 6/2002 | Brisken et al. |
| 2002/0072743 A1 | 6/2002 | KenKnight et al. |
| 2002/0077673 A1 | 6/2002 | Penner et al. |
| 2002/0082583 A1 | 6/2002 | Lerner |
| 2002/0082665 A1 | 6/2002 | Haller et al. |
| 2002/0102707 A1 | 8/2002 | Harrow et al. |
| 2002/0106410 A1 | 8/2002 | Masters |
| 2002/0137014 A1 | 9/2002 | Anderson et al. |
| 2002/1013314 | 9/2002 | Daniel et al. |
| 2002/0177689 A1 | 11/2002 | Benson et al. |
| 2002/0177772 A1 | 11/2002 | Altman et al. |
| 2002/0177782 A1 | 11/2002 | Penner |
| 2002/1017684 | 11/2002 | Slepian |
| 2002/0183682 A1 | 12/2002 | Darvish et al. |
| 2002/0183686 A1 | 12/2002 | Darvish et al. |
| 2003/0028089 A1 | 2/2003 | Galley et al. |
| 2003/0040683 A1 | 2/2003 | Rule et al. |
| 2003/0060753 A1 | 3/2003 | Starkweather et al. |
| 2003/0060765 A1 | 3/2003 | Campbell et al. |
| 2003/0069614 A1 | 4/2003 | Bowman et al. |
| 2003/1007360 | 4/2003 | Pinkerton |
| 2003/0100885 A1 | 5/2003 | Pettis et al. |
| 2003/0130616 A1 | 7/2003 | Steil et al. |
| 2003/0144712 A1 | 7/2003 | Streeter |
| 2003/0167033 A1 | 9/2003 | Chen et al. |
| 2003/0171401 A1 | 9/2003 | Johnson et al. |
| 2003/0176933 A1 | 9/2003 | Lebel et al. |
| 2003/0181852 A1 | 9/2003 | Mann et al. |
| 2003/0181894 A1 | 9/2003 | Neuberger |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0208152 A1 | 11/2003 | Avrahami et al. |
| 2003/0212364 A1 | 11/2003 | Mann et al. |
| 2003/0212441 A1 | 11/2003 | Starkweather et al. |
| 2003/0231990 A1 | 12/2003 | Faries et al. |
| 2004/0014131 A1 | 1/2004 | Benson et al. |
| 2004/0024361 A1* | 2/2004 | Fago et al. .................... 604/152 |
| 2004/0030282 A1 | 2/2004 | Freyman et al. |
| 2004/1002870 | 2/2004 | Pinkerton |
| 2004/1005932 | 3/2004 | Daniel et al. |
| 2004/0062148 A1 | 4/2004 | Skyggebjerg et al. |
| 2004/0063200 A1 | 4/2004 | Chaikof et al. |
| 2004/0064086 A1 | 4/2004 | Gottlieb et al. |
| 2004/0064127 A1 | 4/2004 | Lerner |
| 2004/0064133 A1 | 4/2004 | Miller et al. |
| 2004/0073190 A1 | 4/2004 | Deem et al. |
| 2004/0082639 A1 | 4/2004 | Ho et al. |
| 2004/0092885 A1 | 5/2004 | Duchon et al. |
| 2004/0098113 A1 | 5/2004 | Forsell et al. |
| 2004/1008521 | 5/2004 | Moberg et al. |
| 2004/1011113 | 6/2004 | Shenderova et al. |
| 2004/0127895 A1 | 7/2004 | Flock et al. |
| 2004/0142034 A1 | 7/2004 | Thor et al. |
| 2004/0147872 A1 | 7/2004 | Thompson |
| 2004/0157884 A1 | 8/2004 | Johnson et al. |
| 2004/0171518 A1 | 9/2004 | Van Antwerp et al. |
| 2004/0186533 A1 | 9/2004 | Greenberg et al. |
| 2004/0193090 A1 | 9/2004 | Lebel et al. |
| 2004/0198822 A1 | 10/2004 | Fraser et al. |
| 2004/0209960 A1 | 10/2004 | Burgard et al. |
| 2004/0210267 A1 | 10/2004 | Lebel et al. |
| 2004/1020269 | 10/2004 | Shanley et al. |
| 2004/1020986 | 10/2004 | Landau et al. |
| 2004/0220551 A1 | 11/2004 | Flaherty et al. |
| 2004/0225338 A1 | 11/2004 | Lebel et al. |
| 2004/0230117 A1 | 11/2004 | Tosaya et al. |
| 2004/0236269 A1 | 11/2004 | Marchitto et al. |
| 2004/0248979 A1 | 12/2004 | Brettman et al. |
| 2004/0260239 A1 | 12/2004 | Kusleika |
| 2004/1026535 | 12/2004 | Zhang et al. |
| 2005/0004663 A1 | 1/2005 | Llanos et al. |
| 2005/0008580 A1 | 1/2005 | Gong et al. |
| 2005/0015055 A1 | 1/2005 | Yang |
| 2005/0020577 A1 | 1/2005 | Landau et al. |
| 2005/1000973 | 1/2005 | Kim et al. |
| 2005/0026909 A1 | 2/2005 | Landau et al. |
| 2005/0033148 A1 | 2/2005 | Haueter et al. |
| 2005/0033231 A1 | 2/2005 | Powell |
| 2005/0033370 A1 | 2/2005 | Jelen et al. |
| 2005/0054725 A1 | 3/2005 | Thor et al. |
| 2005/0059938 A1 | 3/2005 | Malisch |
| 2005/0065464 A1 | 3/2005 | Talbot et al. |
| 2005/0065465 A1 | 3/2005 | Lebel et al. |
| 2005/0065556 A1 | 3/2005 | Reghabi et al. |
| 2005/0084477 A1 | 4/2005 | Van Antwerp et al. |
| 2005/0090866 A1 | 4/2005 | Miller et al. |
| 2005/0107353 A1 | 5/2005 | Burgard et al. |
| 2005/0107738 A1 | 5/2005 | Slater et al. |
| 2005/0107743 A1 | 5/2005 | Fangrow |
| 2005/0113798 A1 | 5/2005 | Slater et al. |
| 2005/0124560 A1 | 6/2005 | Sung et al. |
| 2005/0137670 A1 | 6/2005 | Christopherson et al. |
| 2005/1014363 | 6/2005 | Zhang et al. |
| 2005/0148955 A1 | 7/2005 | Chong et al. |
| 2005/0171160 A1 | 8/2005 | Edgar et al. |
| 2005/0171513 A1 | 8/2005 | Mann et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0187140 A1 | 8/2005 | Hunter et al. |
| 2005/1017566 | 8/2005 | Hunter et al. |
| 2005/0192637 A1 | 9/2005 | Girouard et al. |
| 2005/0196421 A1 | 9/2005 | Hunter et al. |
| 2005/0208095 A1 | 9/2005 | Hunter et al. |
| 2005/0217674 A1 | 10/2005 | Burton et al. |
| 2005/0221270 A1 | 10/2005 | Connelly et al. |
| 2005/0222191 A1 | 10/2005 | Falotico et al. |
| 2005/0229931 A1 | 10/2005 | Denyer et al. |
| 2005/0232964 A1 | 10/2005 | Fennimore |
| 2005/0232965 A1 | 10/2005 | Falotico |
| 2005/0239838 A1 | 10/2005 | Edgar et al. |
| 2005/0239890 A1 | 10/2005 | Fraser et al. |
| 2005/1022083 | 10/2005 | Falotico et al. |
| 2005/1022804 | 10/2005 | Thor et al. |
| 2005/0249775 A1 | 11/2005 | Falotico et al. |
| 2005/0249776 A1 | 11/2005 | Chen et al. |
| 2005/0256165 A1 | 11/2005 | Edgar et al. |
| 2005/0256499 A1 | 11/2005 | Pettis et al. |
| 2005/1024584 | 11/2005 | Christopherson et al. |
| 2005/0267550 A1 | 12/2005 | Hess et al. |
| 2005/0270245 A1 | 12/2005 | Villaseca et al. |
| 2005/0272719 A1 | 12/2005 | Landau et al. |
| 2005/0282799 A1 | 12/2005 | Landau et al. |
| 2005/0282859 A1 | 12/2005 | Thor |
| 2005/1027280 | 12/2005 | Falotico et al. |
| 2005/1027684 | 12/2005 | Zhang et al. |
| 2006/0025663 A1 | 2/2006 | Talbot et al. |
| 2006/0030837 A1 | 2/2006 | McKenna et al. |
| 2006/0030838 A1 | 2/2006 | Gonnelli |

(56) References Cited

U.S. PATENT DOCUMENTS

| | | |
|---|---|---|
| 2006/0041243 A1* | 2/2006 | Nayak et al. ............... 604/506 |
| 2006/1002575 | 2/2006 | Francischelli et al. |
| 2006/1003109 | 2/2006 | Cohen et al. |
| 2006/0063754 A1 | 3/2006 | Edgar et al. |
| 2006/0063755 A1 | 3/2006 | Edgar et al. |
| 2006/0063928 A1 | 3/2006 | Edgar et al. |
| 2006/0079858 A1 | 4/2006 | Miller et al. |
| 2006/0079941 A1 | 4/2006 | Ovsyshcher et al. |
| 2006/0094705 A1 | 5/2006 | Edgar et al. |
| 2006/0111704 A1 | 5/2006 | Brenneman et al. |
| 2006/0122863 A1 | 6/2006 | Gottesman et al. |
| 2006/0129050 A1 | 6/2006 | Martinson et al. |
| 2006/0129225 A1 | 6/2006 | Kopia et al. |
| 2006/0142819 A1 | 6/2006 | Penner et al. |
| 2006/1012266 | 6/2006 | Nghiem et al. |
| 2006/0149218 A1 | 7/2006 | Slater et al. |
| 2006/0149339 A1 | 7/2006 | Burnes et al. |
| 2006/0173406 A1 | 8/2006 | Hayes et al. |
| 2006/0173444 A1 | 8/2006 | Choy et al. |
| 2006/0184092 A1 | 8/2006 | Atanasoska et al. |
| 2006/0184154 A1 | 8/2006 | Moberg et al. |
| 2006/0188575 A1 | 8/2006 | Thor et al. |
| 2006/0247311 A1 | 11/2006 | Fraser et al. |
| 2006/0253085 A1 | 11/2006 | Geismar et al. |
| 2006/0264509 A1 | 11/2006 | Fraser et al. |
| 2006/0264894 A1 | 11/2006 | Moberg et al. |
| 2006/0270968 A1 | 11/2006 | Greenberg et al. |
| 2006/0271020 A1* | 11/2006 | Huang et al. ............... 604/890.1 |
| 2006/0271112 A1 | 11/2006 | Martinson et al. |
| 2006/0272652 A1 | 12/2006 | Stocker et al. |
| 2006/0276542 A1 | 12/2006 | Fraser et al. |
| 2006/0293309 A1 | 12/2006 | Thor et al. |
| 2007/0003549 A1 | 1/2007 | Ignatovich et al. |
| 2007/0016163 A1 | 1/2007 | Santini et al. |
| 2007/0016170 A1 | 1/2007 | Kovelman |
| 2007/1000475 | 1/2007 | Coughlin et al. |
| 2007/1000995 | 1/2007 | Srinivas et al. |
| 2007/0026042 A1 | 2/2007 | Narayanan |
| 2007/0030764 A1 | 2/2007 | Skyggebjerg et al. |
| 2007/0033074 A1 | 2/2007 | Nitzan et al. |
| 2007/0038100 A1 | 2/2007 | Nita |
| 2007/0040449 A1 | 2/2007 | Spurlin et al. |
| 2007/0048350 A1 | 3/2007 | Falotico et al. |
| 2007/0051362 A1 | 3/2007 | Sullivan et al. |
| 2007/0053996 A1 | 3/2007 | Boyden et al. |
| 2007/0054319 A1 | 3/2007 | Boyden et al. |
| 2007/0060652 A1 | 3/2007 | Fraser et al. |
| 2007/0060864 A1 | 3/2007 | Redding |
| 2007/0060871 A1 | 3/2007 | Istoc et al. |
| 2007/1005487 | 3/2007 | Pastore et al. |
| 2007/0083258 A1 | 4/2007 | Falotico et al. |
| 2007/0087315 A1 | 4/2007 | Stuart et al. |
| 2007/0088248 A1 | 4/2007 | Glenn et al. |
| 2007/0093752 A1 | 4/2007 | Zhao et al. |
| 2007/0112298 A1 | 5/2007 | Mueller et al. |
| 2007/1009875 | 5/2007 | Falotico et al. |
| 2007/0219480 A1 | 9/2007 | Kamen et al. |
| 2008/0023593 A1 | 1/2008 | Ritota et al. |
| 2008/0200897 A1 | 8/2008 | Hoss et al. |
| 2008/0281297 A1 | 11/2008 | Pesach et al. |
| 2010/0057003 A1* | 3/2010 | Dos Santos ............... 604/114 |
| 2010/0106088 A1 | 4/2010 | Yodfat et al. |
| 2010/0152644 A1 | 6/2010 | Pesach et al. |
| 2010/0286467 A1 | 11/2010 | Pesach et al. |
| 2010/1029255 | 11/2010 | Pesach et al. |
| 2010/0318035 A1* | 12/2010 | Edwards et al. ............... 604/187 |
| 2011/0184342 A1 | 7/2011 | Pesach et al. |
| 2011/0288527 A1 | 11/2011 | Pesach et al. |

FOREIGN PATENT DOCUMENTS

| | | |
|---|---|---|
| EP | 1752174 A1 | 2/2007 |
| FR | 2795629 | 1/2001 |
| WO | WO-00/18339 | 4/2000 |
| WO | WO-00/23132 | 4/2000 |
| WO | WO-00/32259 | 6/2000 |
| WO | WO-00/74763 | 12/2000 |
| WO | WO-00/78212 A1 | 12/2000 |
| WO | WO-01/01852 | 1/2001 |
| WO | WO-01/47408 | 7/2001 |
| WO | WO-01/93931 | 12/2001 |
| WO | WO-02/068028 | 9/2002 |
| WO | WO-03/055384 | 7/2003 |
| WO | WO-03/086534 | 10/2003 |
| WO | WO-2006/049570 A2 | 5/2006 |
| WO | WO-2006/084464 | 8/2006 |
| WO | WO-2006/091650 A2 | 8/2006 |
| WO | WO-2008/051924 A2 | 5/2008 |
| WO | WO-2008/114218 | 9/2008 |
| WO | WO-2008/114220 | 9/2008 |
| WO | WO-2008/114223 | 9/2008 |
| WO | WO-2008/114224 | 9/2008 |
| WO | WO-2009/081262 | 7/2009 |
| WO | WO-2010/052579 | 5/2010 |

OTHER PUBLICATIONS

Bos et al., Biomaterials (2005), 26:3901-3909.
Clarke et. al., (2005), Diabetes Care, 28:2412-2417.
Facchinetti et. al., (2007), Journal of Diabetes Science and Technology, 1:617-623.
Heinemann, (2002), Diabetes Technology & Therapeutics, 5:673-682.
Koivisto et al. (1980), British Medical Journal, 280:1411-1413.
Koivisto et al., (1978), The New England Journal of Medicine, 298:79-83.
Magerl et. al., (1996), Journal of Physiology, 497:837-848.
Midttun et. al., (1996), Clinical Physiology, 16:259-274.
Rebrin et al., (2000), Diabetes Technology and Therapeutics, 2:461-472.
Shumaker et al., (2006), Lasers in Surgery and Medicine, 38:211-217.
Sindelka et al., (1994), Diabetologia, 37:377-380.
European Search Report for EP1315647 mailed Jul. 26, 2013.

* cited by examiner

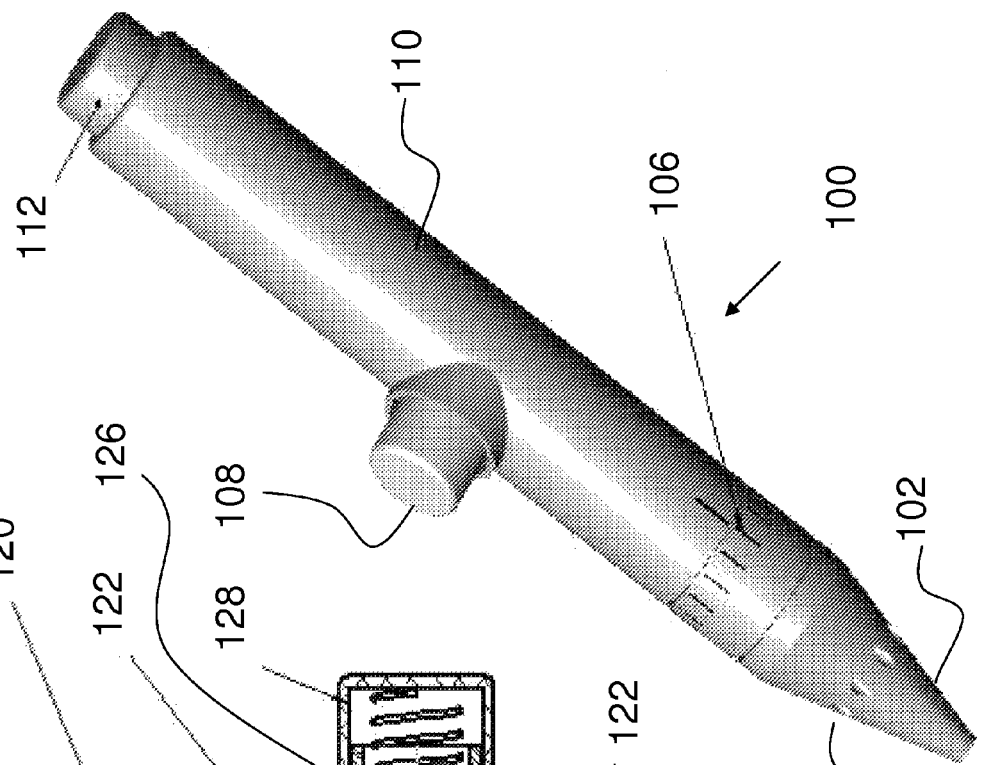
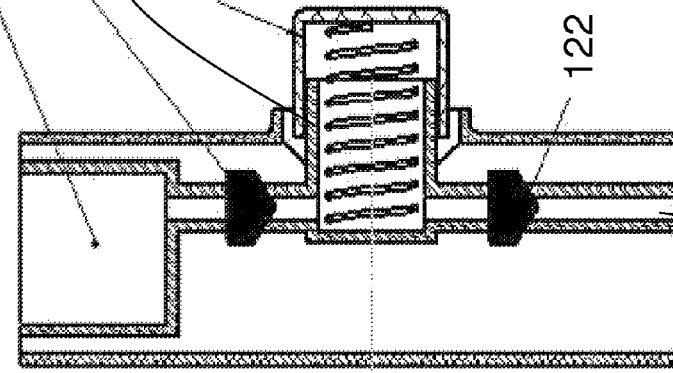
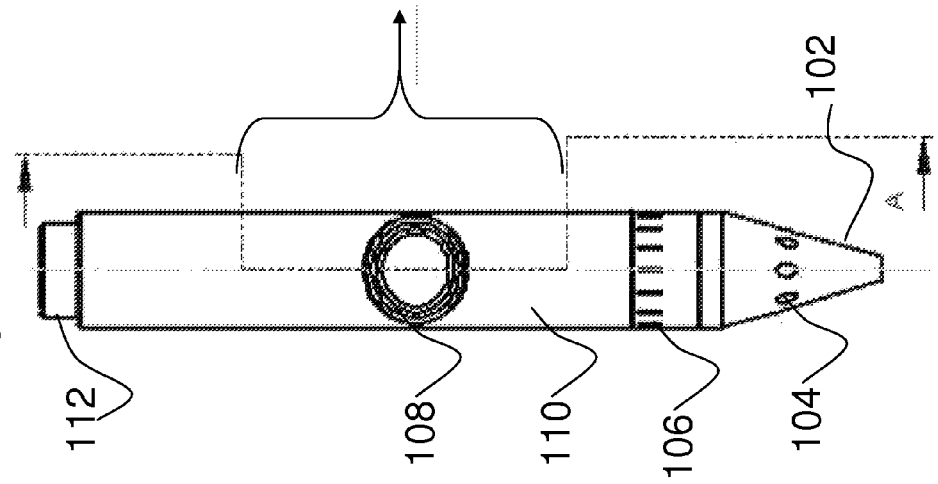

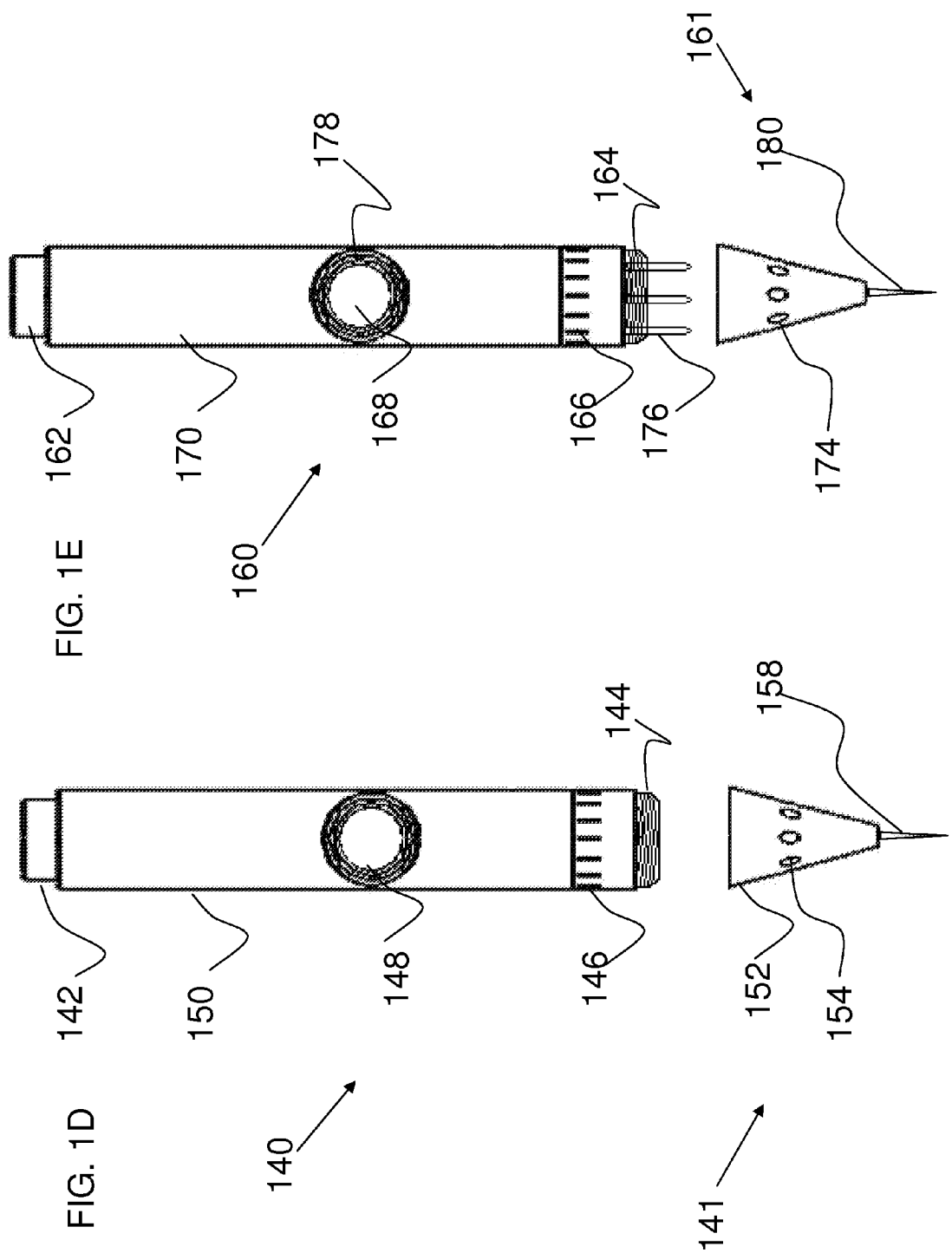

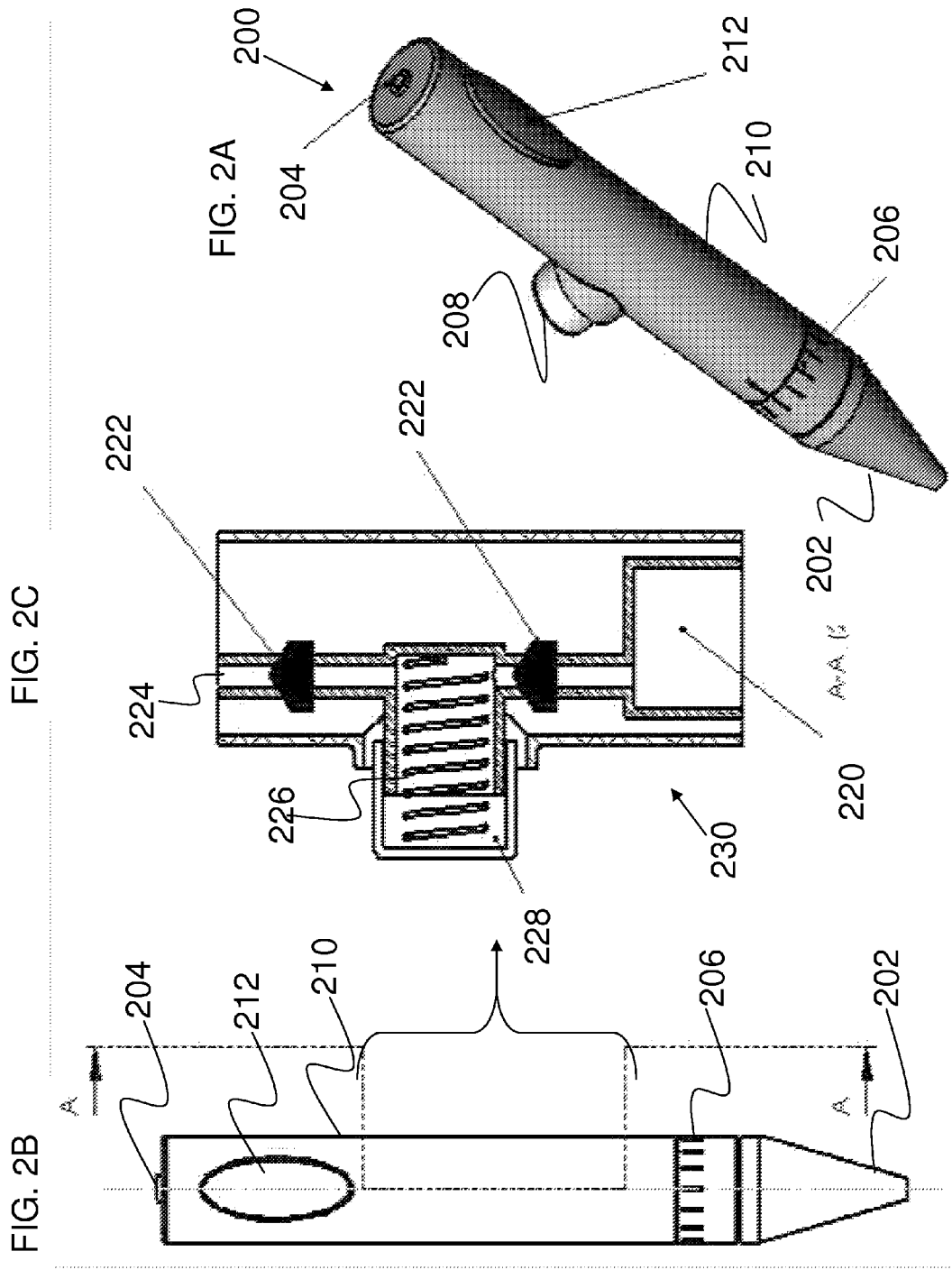

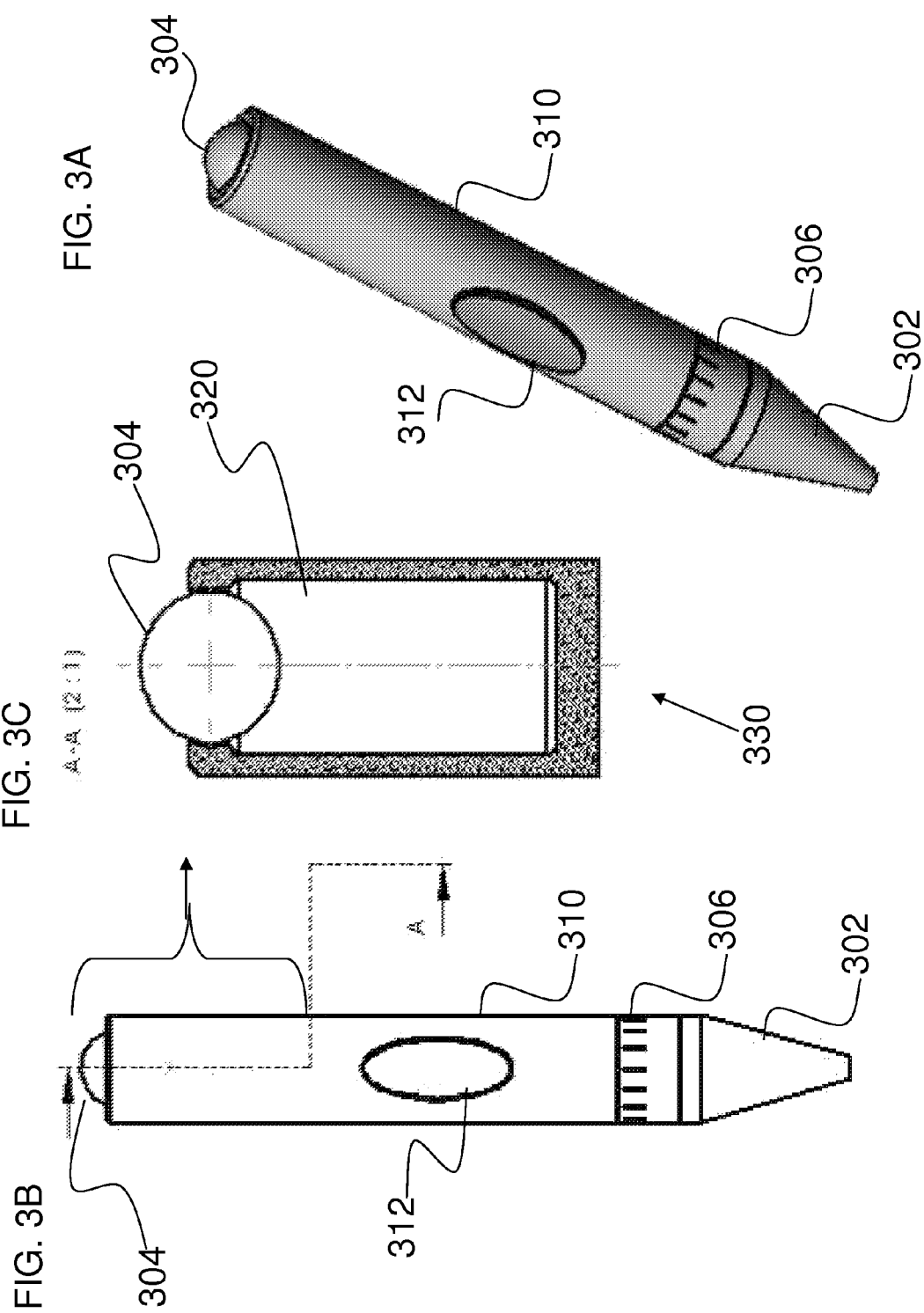

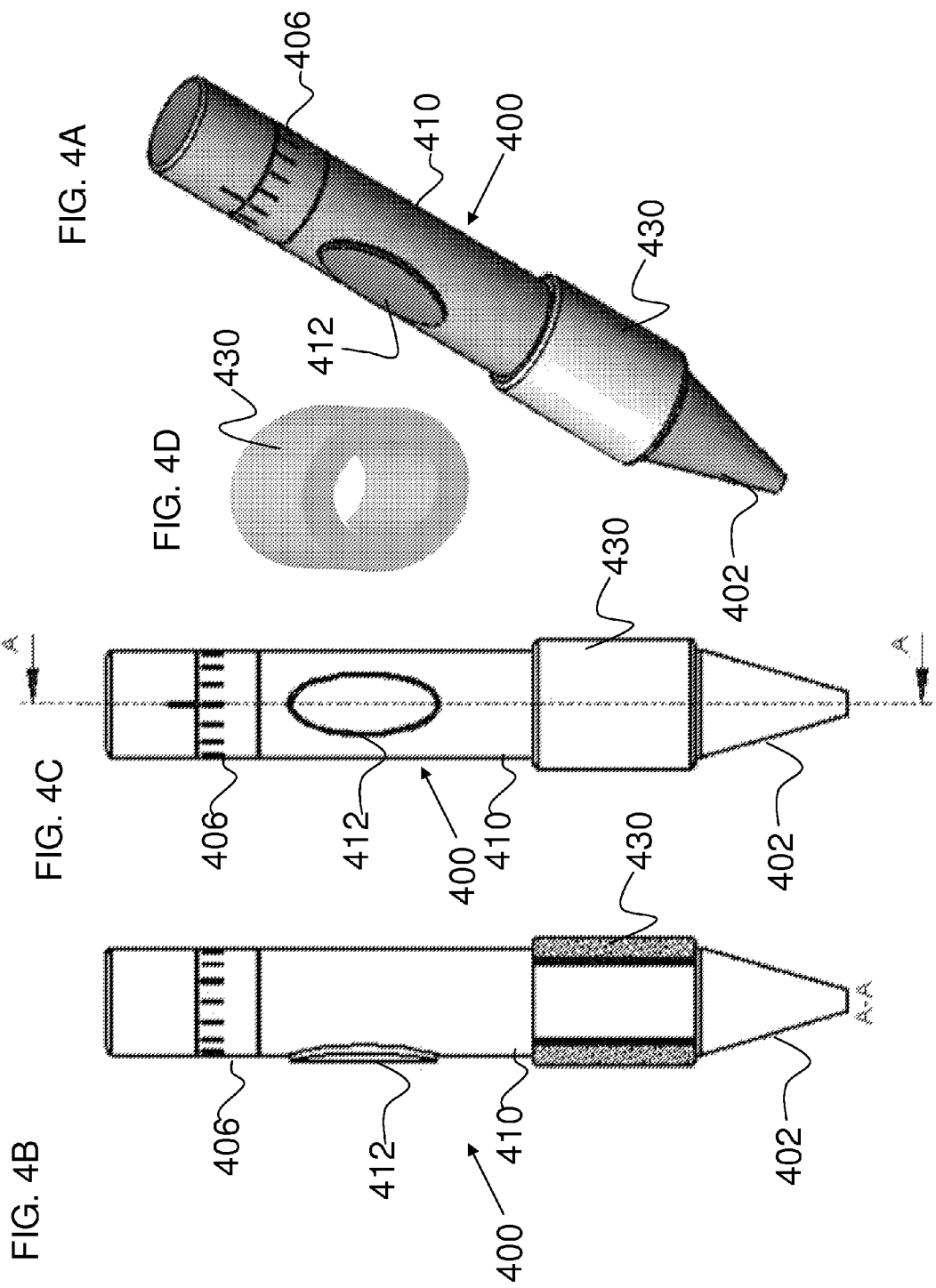

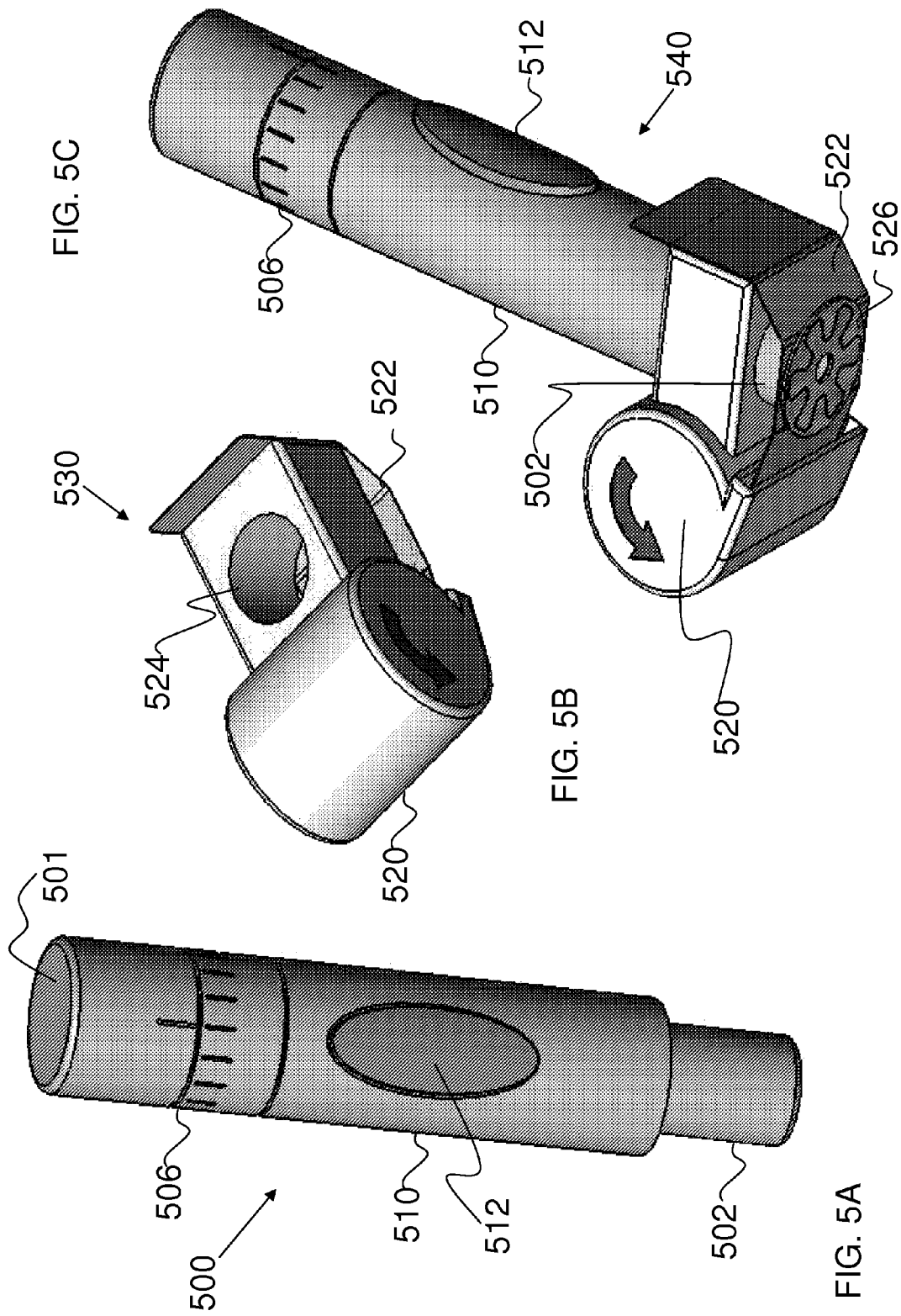

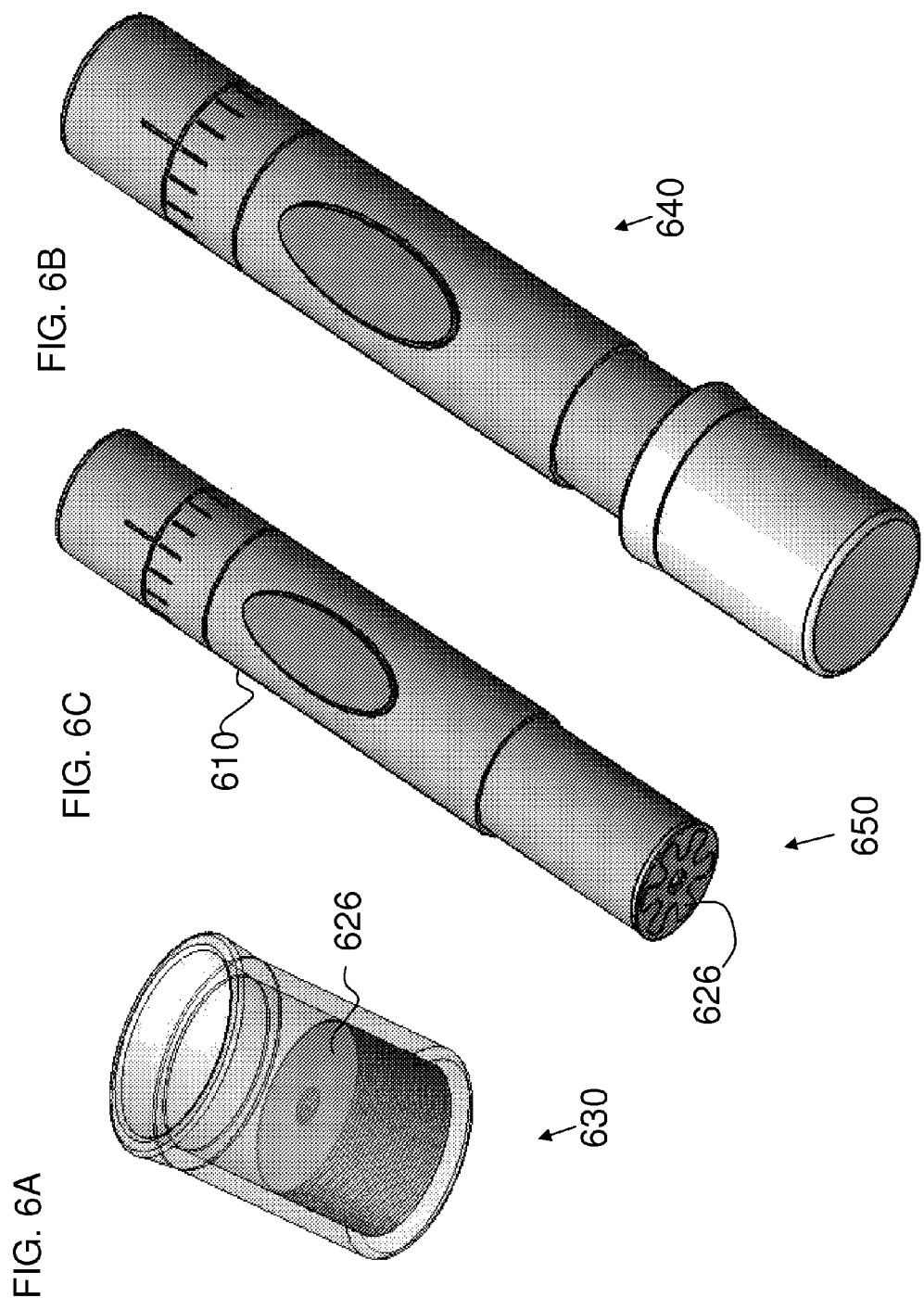

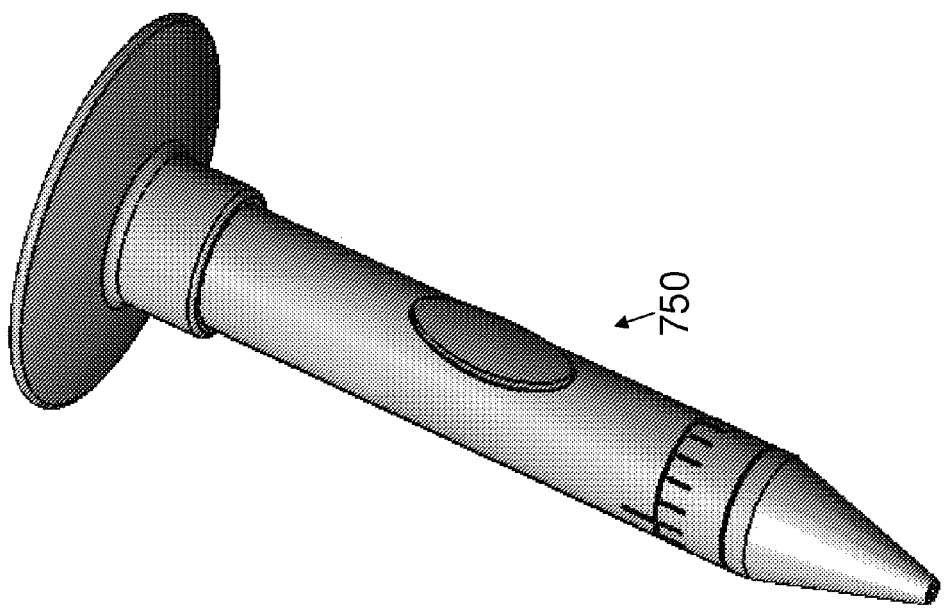
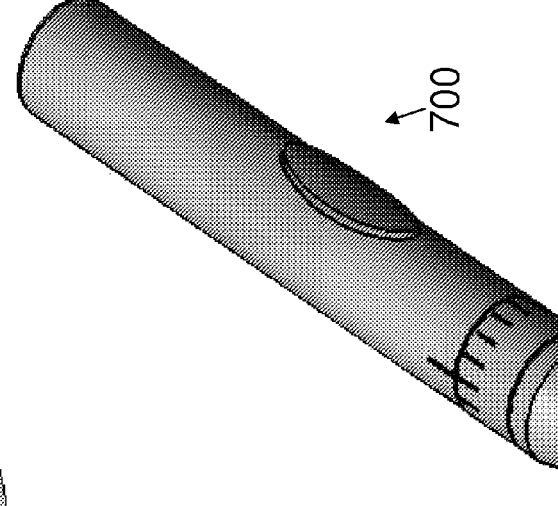
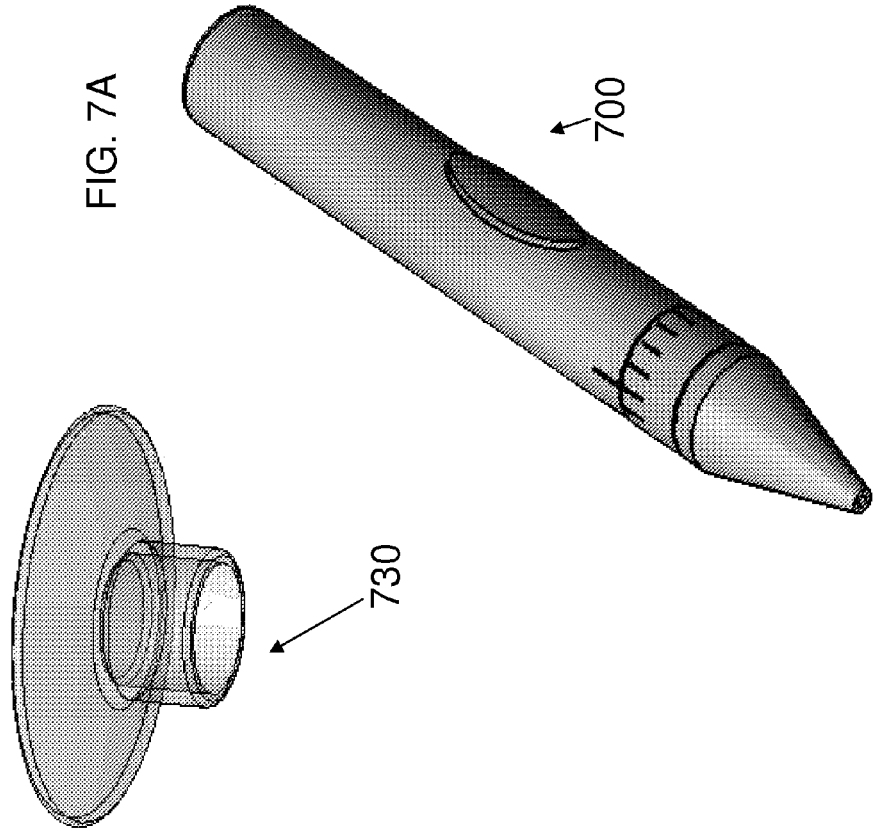

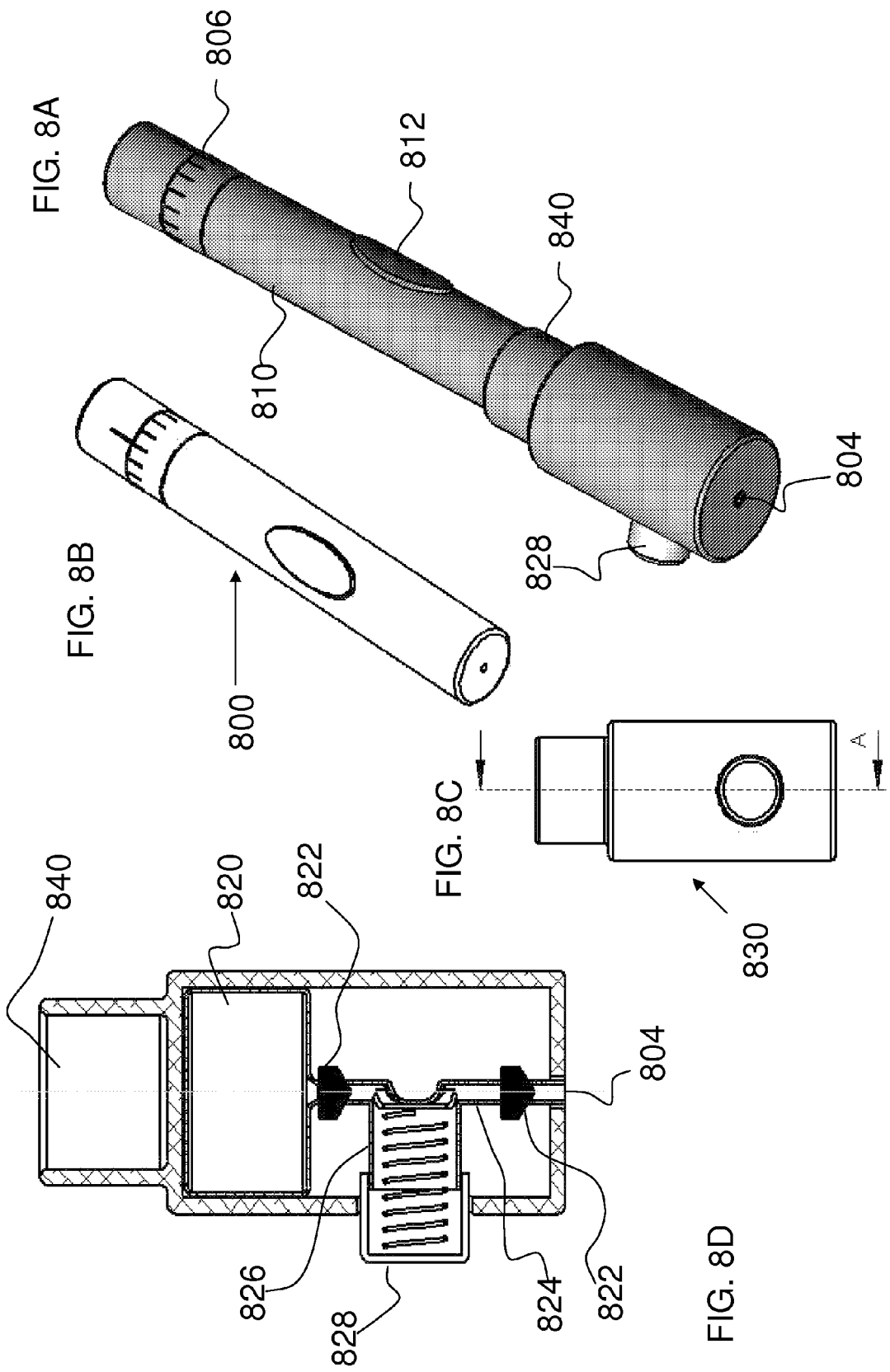

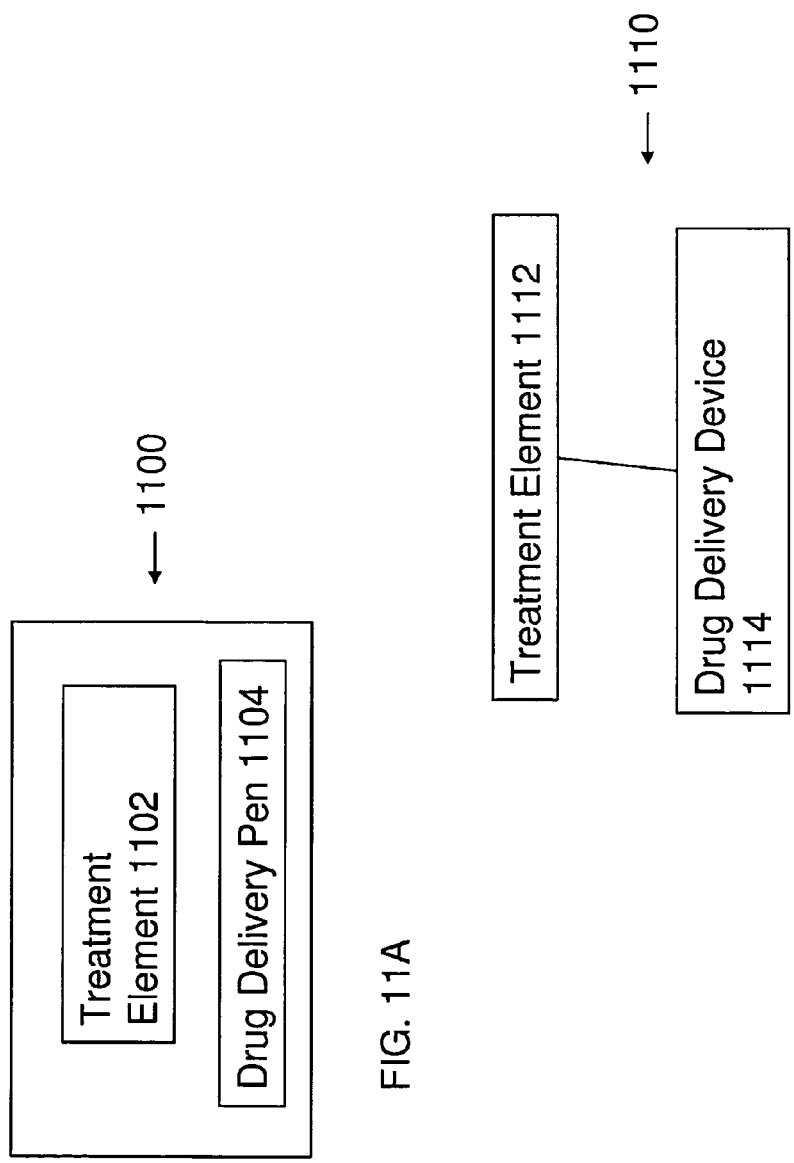

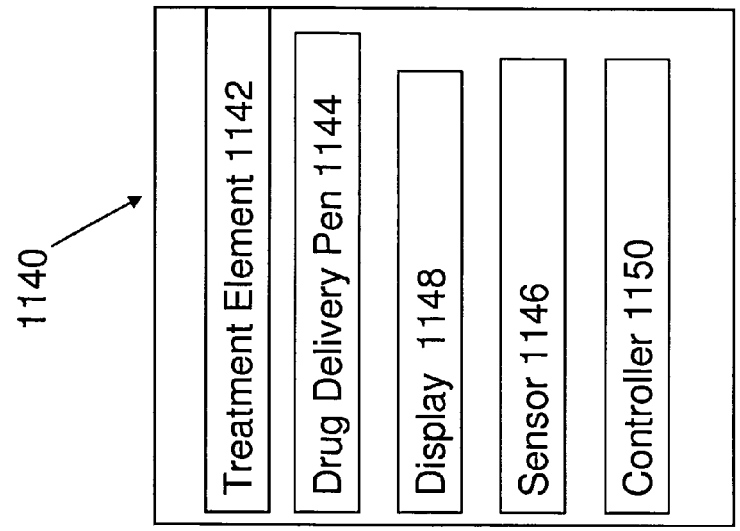
FIG. 11D
FIG. 11C
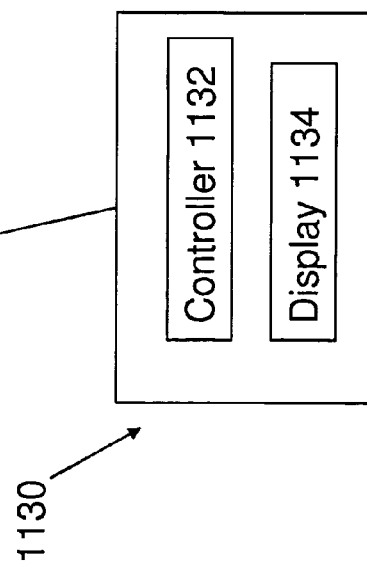

DRUG DELIVERY DEVICE

CROSS-REFERENCE TO RELATED APPLICATION

The present application claims priority to International Patent Application No. PCT/IB2008/051049, to Benny Pesach et al, Mar. 19, 2008, and entitled "DRUG DELIVERY DEVICE". Which claims priority to U.S. Provisional Patent Application No.60/895,518, filed Mar. 19, 2007, U.S. Provisional Patent Application Ser. No. 60/895,519, filed Mar. 19, 2007, U.S. Provisional Patent Application Ser. No.60/912, 698, filed Apr. 19, 2007, U.S. Provisional Patent Application Ser. No. 60/940,721, filed May 30, 2007, U.S. Provisional Patent Application No. 61/016,571, filed Dec. 25, 2007, U.S. Provisional Patent Application No. 61/008,277, filed Dec. 18, 2007 and U.S. Provisional Patent Application No. 61/010, 758, field Jan. 10, 2008, and U.S. patent application Ser. No. 11/812,230, filed Jun. 21, 2007. All of the foregoing disclosures are incorporated herein by reference in their entireties.

BACKGROUND OF THE INVENTION

1. Field of the Invention

The present invention relates to systems and methods for delivering drugs to a patient. In particular, the present invention relates to systems and methods for subcutaneous injection of a medicament and using one or more treatment sources to improve effectiveness of the injected drugs.

2. Background of the Invention

Pen injectors are useful when regular injection by persons without formal medical training occurs. This is increasingly common amongst those having chronic conditions such as diabetes where self-treatment enables such persons effectively manage their condition. Many of the insulin pen injectors are reusable and usually loaded with an insulin cartridge that may be used for a plurality of injections or for a number of days. Many other diabetic patients use regular syringe(s) and needles for insulin injection.

Diabetes is a very serious illness affecting millions of people today. Many diabetic patients require injections of insulin to maintain proper levels of glucose in their blood in order to survive. Such injections of insulin require drug injection systems.

Many medical treatment systems and methods involve drug injection systems that employ subcutaneous injections of therapeutic fluids, drugs, proteins, and other compounds. Such delivery systems and methods, especially for insulin delivery, may use injection pens to inject insulin to the subcutaneous tissue, or regular syringe. In the conventional insulin injection pens, the pen includes a disposable insulin reservoir and a disposable needle through which insulin is injected into the tissue. The needle is a single use needle, while the insulin reservoir can be used for two to three days. In the conventional insulin injection pens, the injection is done by attaching the insulin injection pen to the skin at the injection site and pressing a button that first insert the needle using a spring into the subcutaneous tissue and then inject the insulin to the subcutaneous tissue.

In many instances, the patients require insulin injection around the clock to keep proper levels of glucose in their blood. Two major types of insulin can be injected—a long-acting insulin that provides the basal insulin rate needed for keeping patient's blood glucose in the desired range between meals and over night and an insulin bolus injection that provides an amount of insulin for matching a dose of carbohydrates consumed by the patient.

When patient consumes food, his or her levels of glucose rise. Unfortunately, many conventional subcutaneous injection devices are incapable of quickly matching and/or preventing the rise of blood glucose. The delay in such matching is also true in case of the "rapid-acting" insulin. Some of the reasons for this delay include a lag in the absorption of insulin from the injection site and the time it takes for complex insulin molecules to break down into monomers.

Additionally, since blood glucose levels rise shortly following the meal, the delay in matching insulin to the rising levels causes post prandial hyperglycemic events (i.e., when levels of blood glucose are above normal) to occur. Occasionally, after certain period of time passes (e.g., 2-3 hours) after the meal, the blood glucose levels drop yet insulin concentrations in the blood rise followed by the peak of the systemic insulin effect and may result in causing hypoglycemic events (i.e., when levels of blood glucose are below normal) to occur. Both hyperglycemic and hypoglycemic events are highly undesirable. Additionally, since local blood perfusion at the insulin injection region has large variability, depending on the ambient temperature and other parameters, it induces large variations to the delay of the peak of time profile of the insulin action. Those variations in the insulin peak action period further increase the variability in the blood glucose level.

Thus, it is desirable to provide a system and a method that provides efficient and rapid injection and absorption of the drug to the patient circulatory system. In particular, it is desirable to provide a system and a method for injection of insulin to the patient that improves effectiveness of insulin in the blood to maintain normal levels of blood glucose and prevent or reduce hyperglycemic and hypoglycemic events.

SUMMARY OF THE INVENTION

The present invention relate to systems, devices and methods for injecting a drug, substances and/or chemicals to a patient that further provides a tissue treatment element for improving the effectiveness of drug delivery upon injection. In some embodiments, the present invention relates to a device for improving performance of drug delivery in the form of injection pens or syringes. In general, the present invention's suggested methods and devices can be used in many drug injection devices, such as injection pen(s), syringe(s), or jet injector(s), or other injection devices. As such, although the present application discusses mainly injection pens, it is understood by one skilled in the art that such devices can be used with any other injection devices. In some embodiments, the present invention provides for a device that further provides an additional treatment to a tissue region where the drug is delivered. In some embodiments, the treatment is utilized to improve drug delivery process by improving the drug's pharmacokinetic and/or pharmacodynamic profile. The treatment may come in various forms, for example, including analgesic, vasodilator or the like. The treatment may be any form of treatment that leads to improved vasodilatation of the tissue being injected, including but not limited to, exposing the tissue region to an energy, radiation, heat, mechanical vibrations, suction, massaging, acoustic stimulation, electromagnetic radiation, electric field, magnetic field, electrical stimulation, injection of an additional substance(s), or any combination of the above to improve the drug's pharmacokinetic and/or pharmacodynamic profile. Each treatment type may have a separate protocol in order to evoke the necessary reaction such as vasodilatation or the like.

In some embodiments, the present invention provides a needle free drug delivery pen that is coupled to a treatment element. The treatment element improves the pharmacokinetic and/or pharmacodynamic properties of the drug that is being delivered to the target tissue using a fluid jet. The drug delivery injector for administering a drug, for example, insulin, as a jet nozzle configured for firing insulin in a fluid jet in a configuration and with sufficient velocity to penetrate tissue of the patient to a delivery site. A drug containing compartment is associated with the nozzle for containing the drug and feeding the insulin to the delivery nozzle for injection. A firing mechanism includes an energy source is associated with the drug compartment for forcing the drug through the nozzle at a sufficient velocity to penetrate to the target site. In some embodiments, the energy source producing the fluid jet can be a coil spring, gas spring, or any other spring. A trigger or a dosage release button of the drug delivery injector is movable by the user and associated with the firing mechanism for activating the energy source that produces the drug fluid jet by forcing of the drug through the nozzle once the release button is activated.

In some embodiments, the applied treatment induces vasodilatation through neural stimulation of the tissue of the drug injection site. The neural stimulation can be induced by thermal stimulation and/or mechanical stimulation and/or chemical stimulation. The human neural response to the thermal stimulation includes several mechanisms such as the Nociceptive Axon Reflex that induce vasodilatation among other effects.

In some embodiments, the induced neural response, such as the Nociceptive Axon Reflex, also induces widening of the capillary pores and increasing the capillary wall permeability. This effect is also significant for improving the absorption of the drag through the capillary wall.

In some embodiments, the applied treatment may lead to a reduction in the variability of the drug absorption in the blood or lymph system and its local and systemic effects. For example, heating the tissue region in the vicinity of the area of drug delivery to a preset regulated temperature during and/or after the drug injection and absorption into the blood may cause local blood perfusion at that region to become more reproducible and the drug absorption process more uniform and reproducible as well. Also, by reducing the delay between drug injection into the tissue and absorption into the blood system, the variability of drug action induced by the delayed profile can be reduced. In some embodiments, the temperature of the region adjacent to the injection region can be regulated for longer periods, but the cost may be the energy source volume and weight. Therefore, for minimization of the energy source size, the heating period or heating temporal profile can be optimized in relation to the period of the drug injection and absorption into the blood. In some embodiments, in which the treatment utilized is, for example, heat, the drug interaction with the treatment substance or type will be taken into consideration and can be avoided. For example, a drug's temperature sensitivity will be accounted for so as to avoid protein denaturisation. Insulin is a temperature-sensitive protein and to avoid damage to the insulin the treatment protocol, heating can be limited to ensure the efficacy of the delivered drug. For example, the treatment protocol may control the temperature or the location of the treatment delivery site so as to not damage the drug.

In some embodiments, the neural response that induces vasodilatation is stimulated by applying a mechanical force in the vicinity of the drug infused region, wherein the force includes, but is not limited to, one or more of the following: pressure, massage, vibration, suction and/or any other mechanical stimulation. These tissue treatments or stimulations are known to stimulate the Nociceptive Axon Reflex as well. Among the advantages of the mechanical stimulation is the fact that it does not damage the drug, whereas for example heating insulin above 37° C. may cause damage to it. The calibration of the applied mechanical force may be performed by using one of the procedures discussed above.

In some embodiments, an additional fluid substance can be combined with the drug or, alternatively, injected, infused, or topically applied (which may include transdermal delivery of the drug by permeating through the skin of the patient) to the drug injection site, such that the additional substance induces neural stimulation that leads to local vasodilatation and/or increases of the capillary permeability. The substances can include tolazine, naftidrofuryl, suloctidil, nitroprusside, capsaicin, or any other suitable substance. In some embodiments, an additional substance may induce vasodilatation and improve blood perfusion in the drug infused tissue region. For example, capsaicin stimulates a neural response through the VR1 receptor and produces a similar response to thermal neural stimulation.

The treatment element can be an integral part of the drug delivery injection pen, according to some embodiments of the present invention. In some embodiments, the treatment element can be an auxiliary unit that may be interchanged, replaced, or added to an existing drug delivery injection pen. Such a device can be attached to the drug delivery pen either during or before the drug injection or applied to the drug injection site afterward.

The treatment element, according to some embodiments, may be any one or more of (or a combination of): a heating element, a radiation emitter, a sound transducer, a mechanical/electro-mechanical vibration device, a light emitting device, and an electrode.

In some embodiments, one or more of properties relating to the treatment element may be controlled by a processor in order to achieve a desired response of the tissue region undergoing drug delivery. Such properties include amplitude, phase, frequency, combination of excitation sources, relative ratio and timing between various excitation sources, or any other properties. In some embodiments, the treatment type or sources can be also adjusted according to chemical and/or physical properties of the drug being delivered. The tissue response to the treatment element/stimulation enhances the functionality of the injected drug by enhancing the kinetics of molecular transport from the injection site inside the tissue to various compartments surrounding the tissue region and to the blood system.

In some embodiments, a treatment element or device supplying tissue treatment or stimulation to a tissue region can be configured to monitor and control properties of the treatment source. For example, controllable properties of a treatment protocol include amplitude, phase, intensity, frequency, or any other properties. Further control can be gained by actively monitoring, such that the information is provided to a controller ("controller" or "processing unit") that uses the information to reduce the variability of the drug pharmacokinetics. In such embodiments, the device can be configured to monitor properties of the adjacent tissue, such as local blood perfusion or skin temperature. Based on such monitoring, the information can be provided to the controller that utilizes the information to improve pharmacokinetic or pharmacodynamic profile of the drug as well as its performance and reduce variability of the drug injection process.

In some embodiments, the present invention's device includes a sensor or other triggering input mechanism that is configured to prevent deployment of the drug delivery pen unless certain criteria are fulfilled. Such criteria can include activation of a treatment protocol or element.

In some embodiments, tissue treatment can be applied simultaneously with each injection of the drug delivery. In other embodiments, the tissue treatment or stimulation option may be selected manually by the user. In some embodiments, the user may choose to attach the treatment element to the drug delivery pen. The user can enable or disable mechanically the automatic application of treatment element. The user can activate the treatment device or devices before or after the drug injection to enhance the tissue response to the injected drug. Such activation can be done by pressing a button or a sequence of buttons on the drug delivery pen.

For example, in case of an insulin delivery pen, the pen may have a special button for triggering a "fast bolus" as compared to regular bolus injection provided by the drug delivery injection pen. The fast insulin bolus mode can be configured to start one of the above treatments parallel to the injection of insulin or short time before or after the injection of the insulin bolus for a given period of time. This improves or modifies pharmacokinetics or pharmacodynamics of insulin administration, tissue blood perfusion and/or absorption in the blood of a patient and is highly advantageous when applied in conjunction with high glycemic index foods. Application of a "fast bolus" may be useful for consumption of high glycemic index foods, where larger rapid glucose excursions occurs, but also in most of the cases of using insulin boluses for prandial coverage. In some embodiments, application of a "fast bolus" can be set as the default mode of the drug delivery pen. In some embodiments, the user may apply the tissue treatment or stimulation before the meal to further increase the treatment effect.

In some embodiments, at least one effect of the treatments is to reduce local irritation caused by the infused drug or local inflammation reaction caused by the injection. For example, in case of insulin injection, reducing the period in which the high concentration of insulin remains in the tissue may reduce irritation that may be caused by insulin. It can also reduce unwanted effects of the insulin delivery, such as, lipohypertrophy.

Some embodiments of the present invention also provide methods for improving or modifying a drug's pharmacokinetic or pharmacodynamic profile in order to reduce time to peak action in the blood of the injected material by applying a modulation pattern to the infused drug. With this modulation, the injection drug fluid is slightly moved/pulled in and out of the tissue during or after the drug injection process. In such embodiments, this method may not require an additional device applied to the skin.

In some embodiments, the drug delivery pen can mechanically attach a small disposable device to the skin either before, during or after delivery of the drug. The disposable device can apply a treatment or treatments using at least one of the following sources: a heat source (such as a heat resistor), a suction port, for example activated by a pump, a mechanical vibration source, an ultrasound excitation source, an ultrasound transducer, a light source, a massaging element, electromagnetic radiation source, electric field source, magnetic field source, additional substance and/or a combination of at least two of sources to improve drug pharmacokinetics. In some embodiments, the small disposable device can be attached manually either before or after injection of the drug.

In some embodiments, a device for drug injection includes a disposable injection needle for injecting drug into tissue, a reusable drug delivery pen for inserting the needle into the patient skin or subcutaneous layer and for injection of the drug through the needle into one of the skin and/or subcutaneous tissue layer, a treatment device for applying a specific treatment or stimulation to the drug injected region in order to improve drug's pharmacokinetic, pharmacodynamic profile and/or to increase blood perfusion in that region before, during and/or after the drug injection period to improve drug absorption into the blood system. The needle can be injected automatically at the target site using an automatic needle triggering piston or spring. In some embodiments, the needle can be injected at the target site manually through the action of the user inserting the needle independently.

In some embodiments, a device for drug injection includes an injection catheter for insertion into the tissue, a drug injection device for infusing a drug into the injection catheter, a treatment device for applying a specific treatment or stimulation to the drug infused region in order to improve, modify and/or stabilize the drug pharmacokinetics, pharmacodynamics, and/or to reduce variations of the drug absorption into the blood system.

In some embodiments, a device for drug injection includes at least one of the following: a display, a button, a memory for boluses, a processing unit, a sensor for skin properties, a sensor for treatment level, a glucose sensor, a user interface, wireless connection to a PDA or cell phone for having memory and reminders and remote access to support sites.

In some embodiments, the device for drug/insulin injection includes a glucose sensor. The glucose sensor may measure blood glucose level at alternate sites (for example, at sites with reduced blood perfusion, such as arms and legs). The glucose sensor can be provided on the opposite side the injection end.

In some embodiments, the present invention can be configured for a jet injection. Jet injection involves high pressure injection of material, which obviates the use of needles. This type of injection mode is also referred to as "needle free" or "needleless" injection. In some embodiments, the pen injection device can include a jet injection, in addition to or in place of, the use of one or more needles. Some examples of conventional needle-free injection systems include the MediJector VISION® and some products by Antares. Such systems can be adapted for use with the present invention's jet injection system.

In some embodiments, the injection device includes a disposable nozzle and a reservoir having an additional substance. The reservoir is located at the nozzle and the additional substance is provided in a single use or single dose amount. The reservoir is located within the body of the device and the nozzle features a connector for fluid or other communication with the reservoir.

In some embodiments, rather than disposing a nozzle along with an additional reservoir, an applicator for an additional substance is provided that is attached to or separate from the device. The nozzle can be disposed along with a gauge for adjusting the amount of additional substance to be applied. The applicator may be controlled through a button or other control component. In some embodiments, the gauge can be configured as a ring that can be rotated around the applicator button or other control device to adjust the amount that the button is pressed and/or some function of the other control device and/or to adjust the dose of applied additional substance.

In some embodiments, the drug delivery pen can include an adhesive material, such as a sticker, for assisting the user to create a skin fold for administration of the drug and/or additional substance.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIGS. 1A-E illustrate an exemplary drug delivery pen combined with a mechanism for topical application of an additional substance to the drug injection site, according to some embodiments of the present invention.

FIGS. 2A-C illustrates an exemplary drug delivery pen combined with a mechanism for topical application of an additional substance to the drug injection site, according to some embodiments of the present invention.

FIGS. 3A-C illustrates an exemplary drug delivery pen combined with a mechanism for topical application of an additional substance to the drug injection site, according to some embodiments of the present invention.

FIGS. 4A-D illustrates an exemplary drug delivery pen combined with a mechanism for topical application of an additional substance to the drug injection site, according to some embodiments of the present invention.

FIGS. 5A-C illustrates an exemplary drug delivery pen combined with a mechanism for application of a treatment element on the drug injection site, according to some embodiments of the present invention.

FIGS. 6A-C illustrates an exemplary drug delivery pen combined with a mechanism for application of a treatment element on the drug injection site, according to some embodiments of the present invention.

FIGS. 7A-C illustrates an exemplary drug delivery pen and cover combined with a mechanism for application of a treatment element on the drug injection site, according to some embodiments of the present invention.

FIGS. 8A-D illustrates an exemplary drug delivery pen combined with a mechanism for application of a treatment element on the drug injection site, according to some embodiments of the present invention.

FIGS. 11A-D are block diagrams of exemplary drug delivery devices, according to some embodiments of the present invention.

DETAILED DESCRIPTION OF THE INVENTION

Figure 9A:
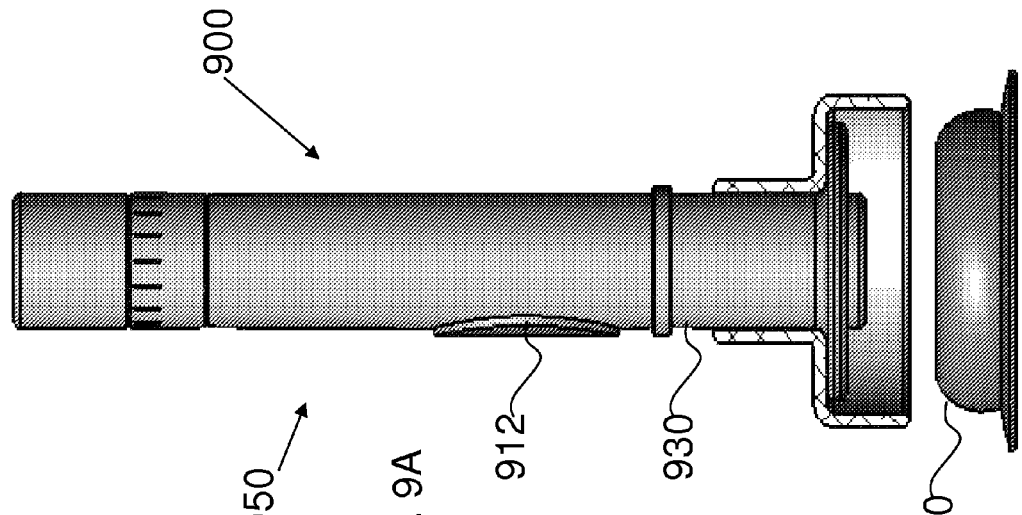
FIGS. 9A-C illustrates an exemplary drug delivery pen combined with a mechanism for application of a treatment element on the drug injection site, according to some embodiments of the present invention.

The present invention relates to a drug delivery pen or other drug injection devices for the injection of a drug at a drug injection site, where the drug in injection device applies a treatment that can improve injected drug's pharmacokinetic and/or pharmacodynamic properties. The following description will refer to a drug injection pen for illustrative, non-limiting purposes, however, as can be understood by one skilled in the art, the present invention is applicable to any other drug injection devices.

FIGS. 1A-C are schematic diagrams of an exemplary drug delivery pen 100 having a treatment element coupled to the delivery pen, according to some embodiments of the present invention. FIGS. 1A and 1B depict an exemplary drug delivery pen 100 having a pen shaft 110, an injection piston release trigger/button 112 (for actuating a piston pump, for example, within the housing of the delivery pen), a treatment release trigger/button 108 (for actuating a pump for delivering the treatment), a needle opening and a housing 102, treatment delivery openings 104, and a drug dosage selector 106. FIG. 1A is a perspective view of the drug delivery pen 100. FIG. 1B is a side view of the pen 100.

The drug delivery pen, for the delivery of insulin, may function as do state of the art drug delivery pens by injecting the selected and determined drug dosage 106 and using injection piston release button 112 to release the piston (not shown) that presses and/or otherwise places pressure on the drug reservoir syringe or vial, for causing injection of the required dosage of drug (not shown) into the targeted area and through needle housing 102. In some embodiments, a fluid jet of the delivered drug can be utilized instead of a syringe to delivery the drug through housing 102 to the targeted delivery site. The drug delivery pen can provide an additional treatment element, such as, an anesthetic, a drug for inducing treatment, a drug for improving effectiveness of the primary drug being injected. The primary drug can be insulin.

The treatment can be delivered over the target tissue using the treatment delivery openings 104, wherein a fluid treatment substance can be applied or sprayed onto the tissue. FIG. 1C is a cross-sectional view of the drug delivery pen 100 showing the treatment element 130 and components thereof. Treatment element 130 includes treatment compartment 120, a plurality of valves 122, a pump 126 and a treatment release button 128. In some embodiments, the treatment compartment 120 stores a formulation of a liquid, ointment, solution, aerosol, foam, solid, gel foam, pressurized liquid, gas, spray, pain reliever drug, analgesic, vasodilatation drug, septic, alcohol, or the like for treatment of the skin tissue area. In some embodiments, treatment may be applied prior to or following deployment of the needle.

Treatment substance stored in compartment 120 can be pumped to the treatment release openings 104 using schematic pump 126 that is activated by pressing treatment release button 128. The treatment release button 128 releases valves 122 to deliver treatment liquid from the compartment 120 through the tube 124 that leads to openings 104. The treatment applied to an area can lead to improved pharmacokinetic and/or pharmacodynamic properties of the primary drug being delivered by way of injection. The pathway by which the pharmacodynamic and/or pharmacokinetic properties of the drug are improved may be dependent on the treatment substance or element utilized.

FIG. 1D is a partial exploded view of a drug delivery pen 140 having a manual injection portion 141, according to some embodiments of the present invention. Pen 140 includes a pen body 150, a dosage release button 142, a treatment release button 148, a drug dosage selector 146, and an injection coupling portion 144. Injection coupling portion 144 is a connection mode to securely affix injection portion 141 to the pen portion 140. The coupling of the injection portion 141 to the pen portion 140 may be accomplished by at least one or more connecting pieces, such as, male/female connectors, threaded connectors, snap connector(s), turn key connectors, hook connectors or any other suitable connectors.

Manual injection portion 141 includes a treatment substance reservoir 152, a treatment delivery opening 154 and a needle 158. The manual injection portion 141 can be disposable after a single use. However, the injection portion 141 can be reusable and can be used a number of times or repeatedly over a period of time. Prior to drug delivery the drug delivery pen body 150 is securely coupled to manual injection portion 141 allowing a user to use the drug delivery pen 140 by selecting a drug dosage using dosage selector 146. Treatment release button 148 triggers the release of the treatment substance from the treatment reservoir 152 through delivery openings 154. The timing of treatment release can be performed prior to, during or following drug delivery, or in a combination thereof. Drug delivery can be accomplished by setting the dosage amount using dosage selector 146, manually inserting needle 158 into the target site, releasing treatment substance through delivery openings 154 and finally delivering the drug with dosage release button 142.

FIG. 1E depicts an additional optional embodiment of the manual drug delivery pen of FIG. 1D. Manual drug delivery pen includes a drug delivery pen housing 160 and manual injection portion 161. Pen housing 160 includes a pen body 170, a dosage release button 162, a drug dosage selector 166, a treatment release button 168, a treatment dosage selector 178, a treatment substance tube 176, and an injection coupling portion 164. The injection coupling portion 164 can be configured to securely affix injection portion 161 to the pen body portion 160. Coupling of the injection portion 161 to pen portion 160 can be accomplished by at least one or more connecting pieces, such as, a male to female connector(s), threaded connectors, snap connector(s), turn key connector(s), hook connectors or any other connection devices.

Manual injection portion 161 is disposable for single use, however, injection portion 161 may be used a number of times, or repeatedly over a continuous period of time. Prior to drug delivery the drug delivery pen body 170 is securely coupled to manual injection portion 161 allowing a user to use drug delivery pen 160 by selecting a drug dosage using drug dosage selector 166. Treatment dosage selector 178 determines the dosage of the treatment substance to be released with treatment release button 168. Pressing treatment release button 168 triggers the release of the treatment substance from the treatment reservoir (not shown) through at least one or more treatment delivery tube 176 that ends in treatment delivery openings 174. Timing of treatment dosage selection and release may be performed prior to, during or following drug delivery, or in a combination thereof. Drug delivery is accomplished by setting the dosage amount using dosage selector 166, manually inserting needle 158 into the target site, releasing treatment substance through delivery openings 174 as described above and finally delivering the drug with dosage release button 162.

FIGS. 2A-C illustrate an exemplary drug delivery pen according to the present invention which is similar to the embodiments depicted in FIGS. 1A-C. In FIGS. 2A-C embodiments, the treatment opening is on the opposite side of the needle housing. FIGS. 2A and 2B depict a drug delivery pen 200 including a pen shaft 210, an injection release button 208, a treatment release button 212, a needle opening and a housing 202, a treatment delivery opening 204 and a drug dosage selector 206. FIG. 2A is a perspective view of the drug delivery pen 200. FIG. 2B is a side view of pen 200.

The drug delivery, such as insulin delivery, functions in a similar fashion as some conventional pens, such as NovoPen, FlexPen, Sanofi Aventis pens or the like, by setting the determined drug dosage 206 and pressing an upper button (not shown in FIGS. 2A-C) that pushes the syringe piston (not shown in FIGS. 2A-C) at the required distance to inject the dosage that was set, such that injection release button 208 is not required. For other pens, such as the Autopen 24, after setting the determined drug dosage 206, the drug is injected by releasing the injection release button 208 which releases the piston (not shown in FIGS. 2A-C) that pushes the syringe piston to the required distance to inject the desired dosage as set by dial 206. In some pens, for drug delivery, the drug is accomplished by setting the determined drug dosage 206 and pressing the needle release button 208, to release the needle (not shown in FIGS. 2A-C) into the targeted area and through needle housing 202, thereby injecting the required drug dosage through that needle. However, the drug delivery pen according to the present invention provides an additional treatment element, such as, in the form of another drug, to induce a treatment for improving the primary drug being injected. The above injection pen's configuration and mechanism as well as other injection devices, such as syringes or jet injectors, can be configured to be used with devices and methods for applying additional treatment to the vicinity of the drug injection site, as described by the present and related applications. In some embodiments, the primary drug can be insulin.

The treatment is delivered over the target tissue using the pen's treatment delivery openings 204, wherein a fluid treatment substance is applied onto the tissue. FIG. 2C is a cross-sectional view of drug delivery pen 200 showing the treatment element 230 and components thereof. Treatment element 230 includes a treatment compartment 220, a plurality of valves 222, a pump 226, a treatment tube 224 and a treatment release button 228. The treatment compartment 220 stores a formulation, a fluid, such as a liquid, ointment, solution, aerosol, pressurized liquid, gas, spray, pain relieve drug, analgesic, vasodilatation drug, septic, alcohol, or the like for treating the skin tissue area. The treatment may be applied prior to or following deployment of the needle, in a two step process one end of the pen for substance treatment delivery using opening 204 and the opposite end for the injection using housing 202.

A treatment substance stored in the compartment 220 can be pumped to the treatment release openings 204 using schematic pump 226 that is activated by pressing the treatment release button 228. The treatment release button 228 releases valves 222 to deliver treatment liquid from the compartment 220 through the tube 224 that leads to the openings 204. In some embodiments, the treatment applied to an area may lead to improved pharmacokinetic and/or pharmacodynamic properties of the primary drug being delivered by way of an injection. The pathway by which the pharmacodynamic and/or pharmacokinetic properties of the drug are improved may be dependent on the treatment substance or element utilized.

FIGS. 3A-C illustrate an exemplary pen-type drug delivery device similar to that described in connection with FIGS. 1A-E and 2A-C, however, in this case, the treatment substance is applied by way of a roller-applicator ball 304 onto the tissue being treated. FIGS. 3A and 3B illustrate similar views of drug delivery pen 300. The drug delivery function of pen 300 is similar to the functions of pens shown in FIGS. 1A-E and 2A-C. The drug dosage can be controlled and determined using a dosage dial 306 that is delivered via the needle housing 302 that encloses a needle (not shown in FIGS. 3A-C), which is triggered using an injection release button 312. A treatment substance may be applied to the injected area either prior to or following injection.

FIG. 3C depicts treatment element 330 including treatment substance container 320 and substance application ball 304. The treatment compartment 320 stores a fluid, such as, a liquid, ointment, solution, aerosol, pressurized liquid, gas, spray, pain relieve drug, analgesic, vasodilatation drug, septic, alcohol, or the like for treating the skin tissue area. Treatment may be applied with a ball 304 prior to or following deployment of the needle, in at least a two-step process one end of the pen for substance treatment delivery using ball 304 the opposite end for the injection using housing 302.

FIGS. 4A-C illustrate another exemplary drug delivery pen 400, according to some embodiments of the present invention. Treatment substance 430 used to improve the pharmacokinetic and/or pharmacodynamic properties of the drug being delivered, such as insulin, may come in the form of a solid, gel, gel form, thixotropic solution or the like. The substance 430 may be applied to a treatment area either prior to or following drug delivery using a needle delivered through needle housing 402. The treatment substance 430 can be a solid, stick, ointment, solution, pain relieving drug, analgesic, vasodilatation drug, septic, alcohol, or the like to treat the skin or tissue area. Substance treatment 430 can be rubbed, rolled over the treated area or applied in any other suitable way.

The drug delivery pen 400 may be manufactured separately from the individual treatment substance 430; alternative, the drug delivery pen 400 may be manufactured along with treatment substance 430 being coupled thereto. FIG. 4D depicts the treatment substance 430 that can be configured to fit over the pen shaft 410 using a sticker, a threading, an adhesive layer, a clip, or any other coupling tools. The pen shaft 410 can be pushed through the lumen of treatment substance 430. The treatment substance 430 can be configured to fit circumferentially around the pen shaft 410. In some embodiments, a single use or a reusable treatment substance 430 can be used with other drug injection devices, such as a syringe.

FIG. 5A illustrates an exemplary drug delivery injectable pen having a needle housing that can accept secondary devices for substance treatment deployment or use, according to some embodiments of the present invention. Drug delivery pen 500 includes shaft 510 that is configured to contain a volume of the injectable drug (such as insulin) for delivery. A dosage dial 506 sets the dosage to be injected with a needle that is injected via an injection release button 520 through the needle and the needle housing 502.

In some embodiments, the drug delivery pen 500 includes a glucose sensor 501 for measuring blood glucose with a finger stick. Glucose sensor 501 can be configured to be on the top of the drug delivery pen 500. The pen 500 can be used to release a needle that is used to draw a drop of blood that may be placed over a finger stick (not shown in FIGS. 5A-C) and is placed over the glucose sensor 501 for reading the glucose levels in the drawn blood sample. Additionally, the drop of blood can be applied to a finger stick like glucose sensor inserted into a glucometer type slit, for example on the top of pen 500 (not shown in FIGS. 5A-C).

FIG. 5B depicts a treatment element apparatus 530 that may be coupled to the drug delivery pen 500, as shown in FIG. 5C, to form drug delivery apparatus 540. The drug delivery apparatus 540 including the treatment element apparatus 530 and drug delivery pen 510 may be single unit.

The treatment element apparatus 530 includes a female connector 524 that can be securely coupled to the needle housing 502, which has a corresponding male connector shape. The coupling can be undertaken by threading, fitting, pin lock assembly, adhesives or any other coupling methods.

The drug delivery pen 530 includes treatment substance dispenser 520 that contains a roll 520 adhered to a plurality of treatment element 526. The treatment element 526 can be securely placed over the end of needle housing 502. The treatment element 526 can be implemented in the form of a pad (e.g., releasing an additional substance), a heating pad, a PCB heating element, an optical treatment element, an electromagnetic radiation treatment element, an electrical current treatment element, an acoustical treatment element, a massaging treatment element or an element related to any of the treatment methods discussed above. The treatment element 526 can deliver treatment to a target tissue prior to injection, following injection, or at the time of injection to improve the pharmacodynamic and/or pharmacokinetic properties of an injectable drug. Treatment element 526 can also include a power source to provide the desired treatment power. Treatment element can include a control element, such as an electrical circuit, to control the treatment profile. Treatment element can be disposable, e.g., single use treatment element, whereby after the treatment profile ends, the user can dispose of the treatment element 526. Treatment element can be reusable, whereby after the treatment profile ends, the user can recharge it, exchange the power source, or exchange only a portion of the treatment element 526 that is disposable and then reload it into a new or the same treatment substance dispenser 520 or a substance dispenser 630 shown in FIG. 6A or any other configuration, as disclosed in the present application.

FIGS. 6A-C illustrate exemplary treatment element dispensers that may be coupled to a drug delivery pen 500, as illustrated in FIG. 5A. FIG. 6A illustrates a treatment dispenser 630 that is an optional alternative to dispenser 530 of FIG. 5B. Treatment dispenser 630 includes stackable treatment elements 626 that may be coupled to the pen drug delivery device. FIG. 6B illustrates how a drug delivery pen is coupled to the treatment element dispenser 630. Once the treatment element dispenser 630 is decoupled from the delivery pen apparatus 650, the needle end of the apparatus is coupled with a treatment element 626. The treatment element 626 is alignable with the needle of drug delivery pen 650. This alignment provides for a drug delivery and treatment apparatus 650 to induce application of treatment using element 626 prior to, following, or at the same time as undertaking drug delivery with the drug delivery pen 600 in a one step process.

In some embodiments, the drug delivery using the pen 600 and evoking treatment using element 626 may be undertaken in a two-step process, where treatment element 626 is coupled to a non-needle end of the drug delivery pen 600. This allows drug delivery and treatment to be performed individually. For example, one can trigger the drug delivery with the injection release button 612 and later evoke treatment using element 626. The reverse is also true where treatment may precede drug delivery.

In some embodiments, the treatment element, such as treatment element 526 (shown in FIGS. 5A-C) or element 626, is coupled to a single use needle that is secured to the pen before each dose injection (as shown in FIGS. 1D and 1E), such that when the needle is inserted into the body, the treatment element is attached to and/or otherwise adheres to or around the injection site, automatically, without the need of additional operations by the user.

For any of the embodiments shown herein, the treatment element may include an energy source, which can provide heat, radiation, mechanical vibrations, suction, magnetic energy, ultrasound, light irradiation, RF irradiation, microwave irradiation, electrical stimulation, or any other form of energy or combinations of those energy sources. For example, the treatment element may include a heater to heat the injection site; or a source of optical energy for the energy source, such as a light source, including but not limited to LEDs or laser diodes for example, with one or more other optical elements; or a micro-wave generator or emitter configured to irradiate the injected region with micro-wave radiation; or a radio frequency electromagnetic radiation generator or emitter configured to irradiate the injected region with radio frequency electromagnetic radiation; or a vibration device configured to vibrate the injected region; or a vacuum device for applying suction to the injected region; or an electric field generator or emitter configured to apply an electric field to the injected region; or a magnetic field generator or emitter configured to apply magnetic field to the injected region; or an acoustic signal generator or emitter configured to apply acoustic stimulation to the injected region.

FIGS. 7A-C illustrates an exemplary drug delivery pen 700 similar to the pens shown in FIGS. 5A-C and 6A-C, that is coupled to a treatment element dispenser 730 as shown in FIG. 7B to create drug delivery and treatment apparatus 750. The apparatus 750 includes a treatment element dispenser 730 at the non needle end of drug delivery pen 700. The apparatus 750 provides the drug delivery pen with an ability to deliver drug(s) in a chosen dosage while providing the treatment element that may improve the pharmacokinetic and/or pharmacodynamic property of the delivered drug. In some embodiments, the user can store his/her treatment element(s) in a special case, or in the case of the drug injection device. Before or after the drug injection, the user inserts the treatment element, as discussed above, into the treatment element dispenser 730 and applies it to the injection site. In some embodiments, the treatment element can have a similar shape as the treatment element dispenser 730 and can be coupled directly to the drug delivery pen 700 without using the treatment element dispenser as an adaptor.

FIGS. 8A-D illustrate an exemplary treatment apparatus, similar to the one shown in FIGS. 1A-3C, according some embodiments of the present invention. FIG. 8A depicts a drug delivery pen 800 used to deliver an injectable drug. FIGS. 8B and 8C are views of the treatment element 830 that can be coupled to the drug delivery pen 800, thus, forming a drug delivery and treatment apparatus, as shown in FIG. 8A. The treatment element 830 can be coupled to the pen 800 via the opening 840 that receives the needle end of the drug delivery pen 800. Treatment element 830 includes a treatment substance compartment 820 that can be utilized to store treatment fluid. The treatment compartment 820 stores a fluid, such as gel, foam, liquid, ointment, solution, aerosol, pressurized liquid, gas, spray, pain relieve drug, analgesic, vasodilatation drug, septic, alcohol, or the like for treating the skin tissue area. Treatment can be applied prior to or following deployment of the needle.

Treatment liquid stored in the compartment 820 can be delivered to the target tissue through the opening 804 using pump 826 that is activated by pressing the treatment release button 828. The treatment release button 828 releases valves 822 to deliver treatment liquid from the compartment 820 through the tube 824 that leads to the opening 804. In some embodiments, the amount of treatment liquid can be preset for a user. In some embodiments, a special dial or other means, (not shown in FIGS. 8A-D, but illustrated in FIG. 1E), may be used to set the amount of applied treatment substance. The treatment applied to an area can lead to improved pharmacokinetic and/or pharmacodynamic properties of the primary drug being delivered by way of injection (e.g., insulin). The pathway by which the pharmacodynamic and/or pharmacokinetic properties of the drug are improved is optional and may be dependent on the treatment substance or element utilized.

Figure 9B:
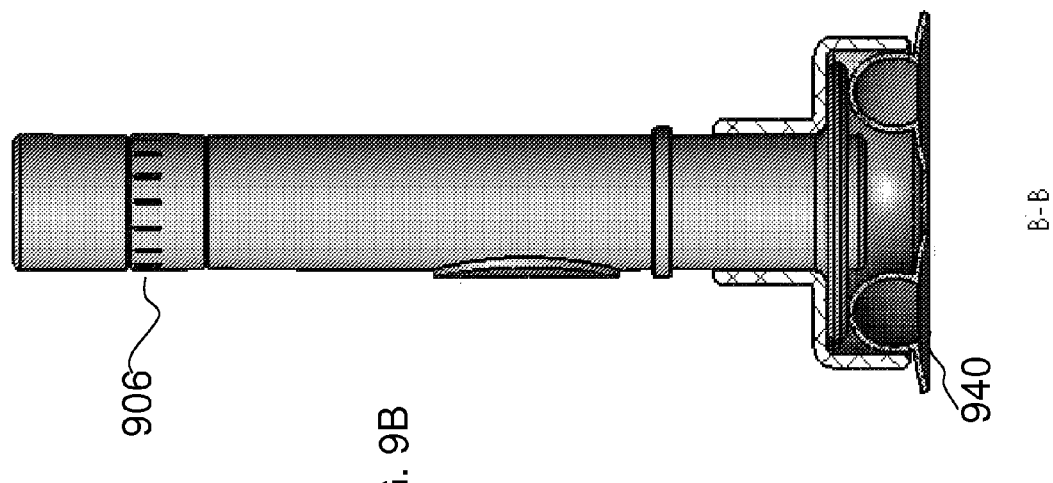
Figure 9C:
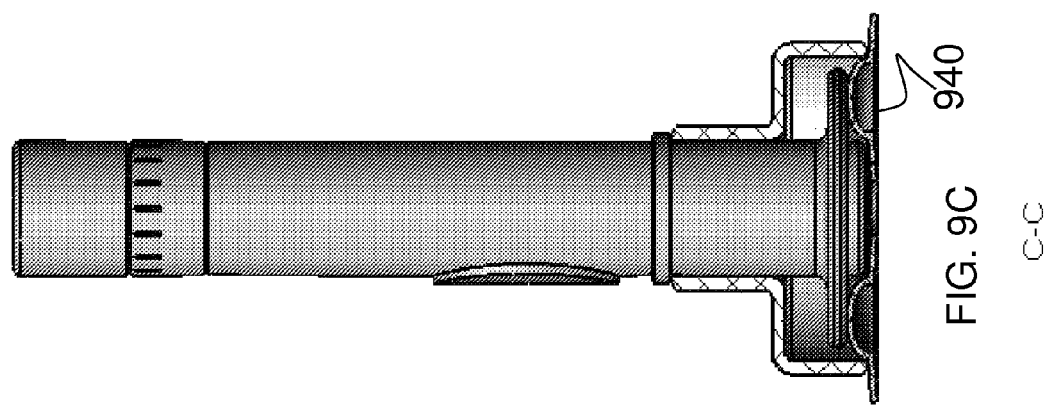

FIGS. 9A-C illustrate the drug delivery pen 900 having the treatment element provide pressure-related treatment, such as suction, massage, or the like, according to some embodiments of the present invention. FIG. 9A depicts a drug delivery pen and treatment apparatus 950 including a drug delivery pen 900 and a treatment element attachment 930 that can be mechanically coupled. The apparatus 950 can be provided as an assembled or unitary drug delivery device. The apparatus 950 can be coupled to the treatment element 940 that is made from a pliable material that can withstand pressure. Such material can be rubber, latex, or any other suitable material configured to create suction over a given treatment area similar to a plunger. The apparatus 950 is placed over the treatment element 940 and is compressed to create further pressure, as shown in FIGS. 9B and 9C, or suction when the pen is lifted. Such suction will bring about vasodilatation in the treated tissue and is configured to improve pharmacodynamics and/or pharmacokinetics of the delivered drug. Drug delivery deployment can be undertaken in the compressed form of the treatment element 940, as shown in FIG. 9C.

Figures 10A, 10B, 10C, 10D, 10E, 10F:
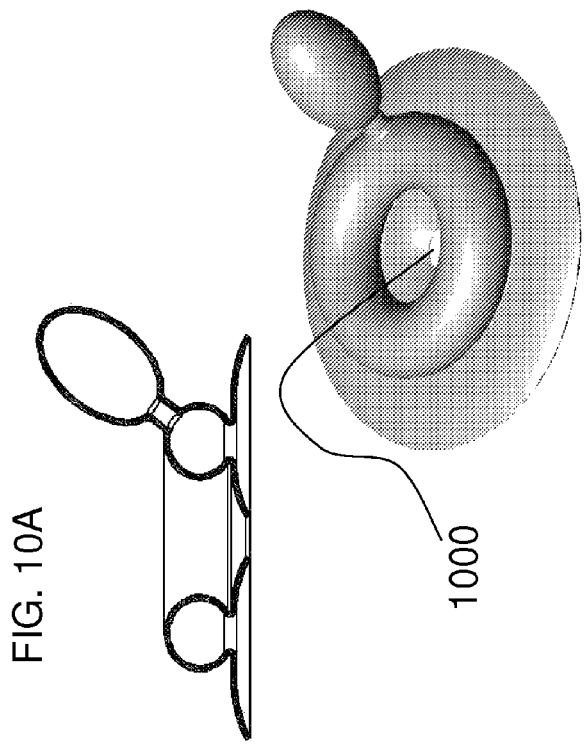
FIGS. 10A-F illustrates an exemplary treatment element that may be coupled to a drug injection at the drug injection site, according to some embodiments of the present invention.

FIGS. 10A-D illustrate a variety of pressure based treatment elements, according to some embodiments of the present invention. FIG. 10A is a cross-sectional view of the treatment element shown in FIG. 10B. The treatment element can be used during drug delivery and includes a lumen 1000 allowing the needle to penetrate through. FIG. 10C is a cross-sectional view of the treatment element shown in FIG. 10D. The treatment element of FIG. 10D can be utilized either prior to or following drug delivery in order to create suction over the tissue area. The treatment elements of FIGS. 10A-D can be used to create suction or vacuum in the vicinity of the drug injection site and to induce local vasodilatation.

FIGS. 10E and 10F illustrate an exemplary treatment element configured as a durable adhesive tape that is used to effectively pinch a fold of skin while maintaining its shape. The treatment element shown in FIG. 10E includes two sticky ends 1050 that are bridged by a malleable section 1052. Each one of the ends 1050 is placed over a patch of skin where an injection for example with a syringe or a drug delivery pen is to be undertaken. Once in place, the ends 1050 are pushed toward each other by the malleable section 1052 to form a bell type shape. Section 1052 can be manufactured from a strong malleable material that can hold its shape, while being repeatedly formed and deformed. FIG. 10F depicts the treatment element of FIG. 10E in a folded form. Section 1052 can be moulded and reshaped forming a treatment element for example to bring about vasodilatation.

FIG. 11A is a block diagram of an exemplary drug delivery apparatus 1100 having a treatment element 1102 incorporated into a drug delivery pen 1104, wherein the treatment element is integrated into the drug delivery pen, according to some embodiments of the present invention. FIG. 11B is a block diagram of an exemplary drug delivery apparatus 1110 having a treatment element 1112 and a drug delivery device 1114 that are removably coupled to each other, according to some embodiments of the present invention. The drug delivery device 1114 or treatment element 1112 can function independently of one another and can be securely coupled to each other to form a single drug delivery and treatment apparatus 1110, similar to the embodiment of FIGS. 4A-6C. Drug delivery device 1114 can be implemented as a syringe, drug delivery pen, drug delivery jet injector or the like.

FIG. 11C is a block diagram of an exemplary drug delivery and treatment apparatus that further includes a sensor 1126, such as a glucose stick sensor, for measuring blood glucose. The drug delivery apparatus 1120 communicates with an external processing unit 1130. The processing unit can be a PDA, a cellular phone, a computer, a laptop or any other device. The unit 1130 includes a controller 1132 and a display 1134. The controller 1132 controls analysis of data received from the drug delivery apparatus 1120 to determine treatment or dosage form or the like related to the functioning of drug delivery pen 1124, and treatment element 1122. The processing unit 1130 provides the user with data regarding historical and current use of the drug delivery apparatus 1120.

FIG. 11D is a block diagram of an exemplary drug delivery device similar to the device shown in FIG. 11C, where the drug delivery apparatus 1140 has an integrated sensor 1146, a processing unit 1150 and a display 1148, according to some embodiments of the present invention. This allows the user to fully control, visualize all activity related to the drug delivery pen 1144 or the treatment element 1142.

Figure 12C:
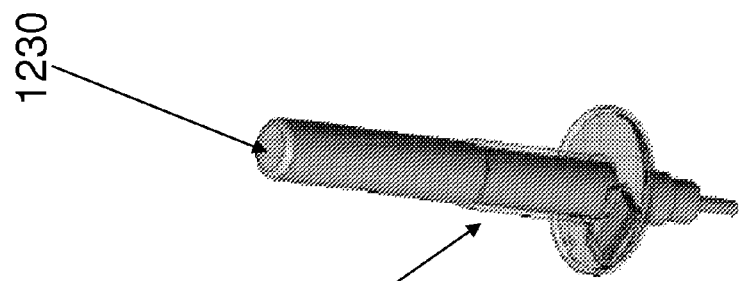
FIGS. 12A-C illustrate an exemplary drug delivery pen combined with a mechanism for application of a treatment element on the drug injection site, according to some embodiments of the present invention.
Figure 12B:
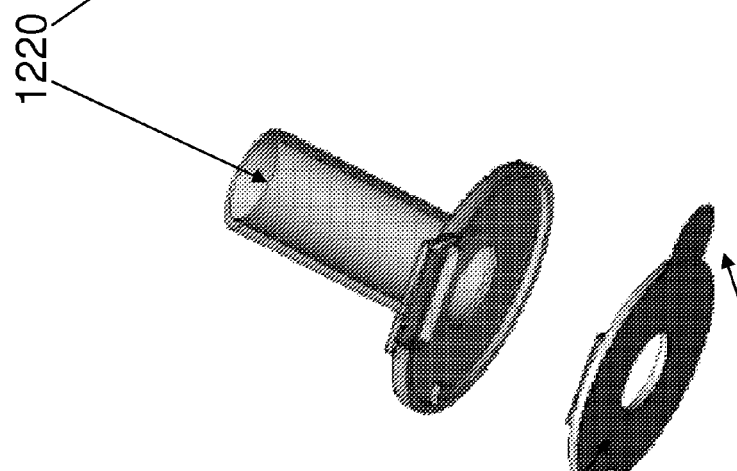
Figure 12A:
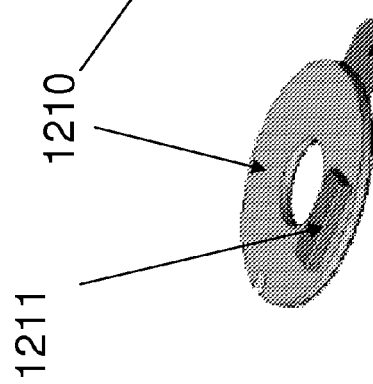

FIGS. 12A-C schematically illustrate exemplary treatment element dispensers that may be coupled to a drug injection device 1200 (as shown in FIG. 12C), according to some embodiments of the present invention. FIG. 12A illustrates a treatment element 1210 with a power source 1211. In some embodiments, the treatment element 1210 includes a power source and a control element to control a treatment profile. For instance, in case of heating, treatment element 1210 can include a heater to heat the tissue around the injection site to a temperature that improves drug's pharmacokinetics and pharmacodynamics. In case of temperature sensitive drugs, such as insulin, treatment element 1210 can include a heater to heat the tissue around the injection site to a temperature that improves drug's pharmacokinetics and pharmacodynamics, without heating the drug above a limiting temperature that may degrade it, such as 37° C. in the case of some types of insulin. Treatment element 1210 may include also an adhesive layer on its bottom side covered with a laminate 1212.

In some embodiments the user has a case with one or few treatment elements 1210. When the user wants to use treatment element over drug injection site, the user takes adaptor 1220, which can be stored in the same case or a different one, and attaches one treatment element 1210 to adaptor 1220, as shown in FIG. 12B. Treatment element 1210 can be attached to adaptor 1220 with a weak mechanical locking, such as a plastic clip, or weak adhesive or other ways known in the art. Then laminate 1212 can be removed. Afterwards, adaptor 1220 is assembled or threaded over drug delivery pen or syringe 1230, as shown at FIG. 12C. In some embodiments needle cap 1231, can be removed from the needle. Then, the needle is inserted into injection site tissue, the drug injection device is operated and the drug is injected through needle into the tissue. During that time, or slightly before or after adaptor 1230, is pushed down to the tissue and treatment element 1210 is attached to the tissue around drug injection site.

In some embodiments, the attachment of treatment element 1210 to the tissue is configured to activate it automatically and the treatment starts according to a predetermined treatment profile. This function can be performed, for example, by a small switch which is pressed when treatment element 1210 is attached to the tissue. In some embodiments, the treatment element 1210 can be activated manually. In some embodiments, treatment element can be controlled and/or programmed for a specific treatment element through a remote control or a connection to its case. Afterwards, the injection device 1230 and the adaptor 1220 are lifted off, either together or separately, and the treatment element 1210 is left attached to the tissue and applies treatment to the vicinity of the drug injection site. The user can remove treatment element after treatment ends or later on. In some embodiments, the treatment element includes an indicator for the user that indicates the beginning of the treatment and the end of the treatment. In some embodiments, the treatment element 1210 may be disposable.

In some embodiments, the treatment element's 1210 power source 1211 may be rechargeable, so that after the treatment ends and the user removes it from the skin, it can be put back to the case and/or placed in a charging cradle for recharging which may be disposed in said case. In some embodiments, the treatment element 1210 may have a disposable portion and a reusable portion. In some embodiments, the drug injection device and at least one treatment element are disposed in the same case prior to injection. This provides additional comfort for the user and allows the user to use both of them together or one after the other.

Figure 13:
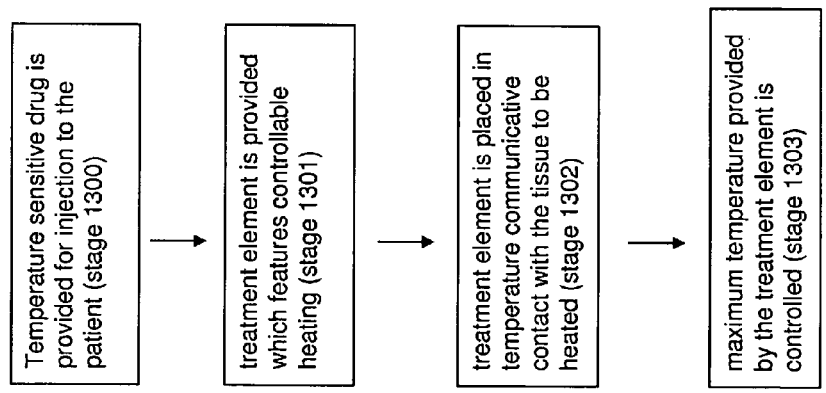
FIG. 13 is a flow chart illustrating an exemplary method for controlling temperature of heating that is provided by a treatment element in order to prevent degradation of a temperature sensitive drug.

FIG. 13 is a flow chart depicting a method for controlling the temperature of heating provided by a treatment elements that heat the injection site tissue vicinity in order to prevent degradation of a temperature sensitive drug. As shown in step 1300, a drug is provided for injection to the patient, where the drug is sensitive to degradation above a limiting temperature. In step 1301, a treatment element is provided that features a controllable heating through a controllable heating element. In step 1302, the treatment element is placed in thermal contact with the tissue to be heated, such that heat from the treatment element is transferred to the tissue to be heated.

In step 1303, a maximum temperature provided by the treatment element is controlled, such that the temperature experienced by the drug (that is, in the environment of the drug) does not exceed the limiting temperature sustainable by the drug before degradation occurs. In some embodiments, the maximum temperature can be calibrated for each drug and/or class of drugs. For example, for some types of insulin, the limiting temperature is about 37° C.

In some embodiments, such control can be provided through a microprocessor or other processor for controlling the temperature output by a heating element. A sensor can be provided in order to measure the temperature at and/or near the tissue being heated, in order to determine the temperature experienced by the drug.

The treatment element includes one or more materials capable of generating an exothermic reaction, in which the amount of such materials and/or ratio can be calculated in order for the temperature of the reaction not to exceed the maximum temperature set for the treatment element based on the desired limiting temperature of the drug. The exothermic reaction can be a heat-generating oxidation reaction, for example, with a mixture of iron powder, activated carbon, salt and water. As can be understood by one skilled in the art, other such mixtures of materials can be used.

In some embodiments, the treatment element and the drug delivery pen are not disposed in the same housing. However, in such cases the user may forget to apply the treatment to the injection site in some cases, thereby changing the pharmacokinetics, which is undesirable. Therefore, to prevent that the drug delivery pen can include a mechanism for reminding the user to apply the required treatment, before, during or after injecting the drug into the tissue. In some embodiments, the drug delivery pen includes a mechanism that identifies whether the treatment was applied or not and permits drug injection only when the tissue treatment was applied. In some embodiments, the drug delivery pen includes, in addition to the drug injection mechanism, a sensor that indicates whether the treatment was applied or was not applied and a processing unit that enables injection of the drug only when the tissue treatment was applied. Such sensor can be an optical sensor that measures optical properties of the local tissue, or Laser Doppler Flowmeter ("LDF") that can measure local blood perfusion and identify that the vasodilatation inducing local treatment was applied and that the treatment level was adequate.

Example embodiments of the methods and components of the present invention have been described herein. As noted elsewhere, these example embodiments have been described for illustrative purposes only, and are not limiting. Other embodiments are possible and are covered by the invention. For example, at the present application many of the suggested methods and devices can be used for many of the drug injection devices, such as injection pens or syringes or jet injector and other known in the art injection devices, so although the examples are mainly given for injection pens they are applied to the other injection devices as well. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

Any and all references to patents, patent applications, articles and other published and non-published documents made in the present disclosure are herein incorporated by reference in their entirety.

What is claimed is:

1. An apparatus for delivering therapeutic fluid to a patient at an injection site, comprising:
a fluid injection device having a housing, wherein the housing includes: an injector for injecting the therapeutic fluid to a bodily tissue of the injection site; and a reservoir for containing the therapeutic fluid; and a treatment element comprising a heater coupled to the fluid injection device and configured to modify the temperature of the bodily tissue in a vicinity of the injection site to improve pharmacokinetic and/or pharmacodynamic property of the injected therapeutic fluid in the bodily tissue either a short time before, during and/or following injection of the therapeutic fluid into the patient, wherein the treatment element does not heat the therapeutic fluid above a predetermined limiting temperature.

2. The apparatus according to claim 1, wherein the fluid injection device is selected from a group consisting of: a syringe, an injection pen, and a jet injector.

3. The apparatus according to claim 1, wherein the treatment element is coupled to the fluid injection device using an adaptor.

4. The apparatus according to claim 3, wherein the treatment element is coupled to the fluid injection device either before or during injection of the therapeutic fluid.

5. The apparatus according to claim 1, wherein the treatment element and the fluid injection device are disposed in the same housing before injection.

6. The apparatus according to claim 1, wherein said treatment is applied to the vicinity of the injection site only during or following the injection of the therapeutic fluid into the patient.

7. The apparatus according to claim 1, wherein the treatment element is configured to apply treatment in order to perform at least one of the functions selected from a group consisting of: enabling a faster onset of action of the therapeutic fluid infused into the infused region, enabling a faster peak of action of the therapeutic fluid injected into the injection site, enabling a faster clearance of the therapeutic fluid from the injection site and into a circulatory system of the patient, improving the repeatability of the pharmacokinetic and/or pharmacodynamic profile in response to the injection of the therapeutic fluid, reducing a variability of absorption of the therapeutic fluid into the blood system and/or lymphatic system of the patent, reducing a variability of onset of action of the therapeutic fluid, reducing a variability of time to peak of action of the therapeutic fluid, and reducing a variability of the clearance of the therapeutic fluid from the injection site and into the circulatory system of the patient.

8. The apparatus according to claim 1, wherein the therapeutic fluid is configured to be injected subcutaneously and further configured to have a systemic effect.

9. The apparatus according to claim 1, wherein the therapeutic fluid is selected from a group consisting of: insulin, insulin analogues, and insulin mimetics.

10. The apparatus according to claim 1, wherein the treatment element is configured to heat the tissue vicinity without heating the vicinity of the injection site to a temperature above a limiting temperature that may damage the therapeutic fluid.

11. The apparatus according to claim 10, wherein the apparatus is configured to improve a clinical outcome of an IDDM patient, wherein the therapeutic fluid is a mixed rapid-acting insulin configured to provide an optimal insulin pharmacokinetic profile to better utilize the faster insulin absorption induced by the treatment.

12. The apparatus according to claim 10, wherein the apparatus is configured to improve a clinical outcomes of an IDDM patient, wherein the treatment is configured to be applied only for carbohydrate rich meals.

13. The apparatus according to claim 10, wherein said heater is U shaped or round.

14. The apparatus according to claim 1, wherein the limiting temperature is approximately 37 degrees C.

15. The apparatus according to claim 1, wherein the apparatus is configured to improve a clinical outcome of an Insulin-Dependent Diabetes Mellitus ("IDDM") patient, wherein the therapeutic fluid is a rapid-acting insulin, the treatment element is configured to heat the skin to a temperature in a range of 37-39° C. at least 1 cm apart of the injection site for a period of time in a range 10-90 min from the time of injection.

16. The apparatus according to claim 1, further comprising a processing unit for controlling the treatment element and configured to control at least one of an amplitude, duration, phase, intensity, and frequency of the treatment applied by the treatment element.

17. The apparatus according to claim 16, further comprising a sensor for detecting the injection of the therapeutic fluid, wherein the treatment element is configured to apply the treatment to the injection site following the detecting by the sensor.

18. The apparatus according to claim 1, wherein the treatment element includes a heater and is configured to regulate heating of the infused region to stabilize its temperature at a pre-determined temperature in order to stabilize pharmacokinetics of the infused therapeutic fluid.

19. The apparatus according to claim 1, wherein the applied treatment is selected from a group consisting of: heating, cooling, intermittent temperature change, optical radiation, micro-wave, radio frequency, electromagnetic radiation, vibration device, physical stimulation, massage the infused region, suction, vacuum, electric field, magnetic field, acoustic signal, ultrasound, and application of one more additional substances to modify the infused substance pharmacokinetics, and/or a combination of at least two of the above treatments.

20. The apparatus according to claim 1, further comprising a treatment release trigger for actuating treatment delivery via said treatment element.

21. The apparatus according to claim 1, wherein the housing further comprises at least one treatment delivering opening for application of treatment to the injection site.

22. The apparatus according to claims 1, further comprising a treatment selector configured to apply a predetermined amount of a treatment substance to at least one of the injection site and adjacent the injection site;
   wherein said treatment substance is selected from a group consisting of: a liquid, ointment, solution, aerosol, foam, solid, gel foam, pressurized liquid, gas, spray, pain reliever drug, analgesic, vasodilatation drug, septic, alcohol, and any combinations thereof.

23. The apparatus according to claim 22, wherein the treatment selector is configured to apply said treatment to at least one of the injection site and adjacent the injection site, wherein said treatment is selected from a group consisting of: radiation, heat, mechanical vibrations, suction, massaging, acoustic stimulation, electromagnetic radiation, electric field, magnetic field, electrical stimulation, injection of additional substance(s), and any combination of the foregoing.

24. The apparatus according to claim 1, wherein the housing further comprises a nozzle through which the therapeutic fluid is injected to the injection site.

25. The apparatus according to claim 1, wherein the treatment element is reusable.

26. The apparatus according to claim 1, wherein the treatment element is disposable.

27. The apparatus according to claim 1, wherein the treatment element has a disposable portion and a reusable portion.

28. The apparatus according to claim 1, wherein the treatment element includes an opening for allowing the injector to be positioned therethrough.

29. The apparatus according to claim 1, wherein said treatment element is further configured to be coupled to the injection site upon being detached from the fluid injection device.

30. The apparatus according to claim 1, wherein the treatment element includes a one or more adherable portions for adhering to the skin adjacent an injection site, and includes a malleable portion.

31. The apparatus according to claim 1, wherein the treatment element is configured to apply one or more additional substances in the vicinity of the injection site, wherein the treatment element is selected from the group consisting of: an injector, a nozzle, an opening and a roller-applicator ball, dispenser.

32. The apparatus according to claim 1, further comprising a remote control unit to control application of treatment by the treatment element.

33. A method for delivering a therapeutic fluid to an injection site on a patient using a fluid delivery device having a fluid injection device having a housing, wherein the housing includes an injector for injecting the therapeutic fluid to a bodily tissue of the injection site and a reservoir for containing the therapeutic fluid, and a treatment element, comprising a heater, coupled to the fluid injection device and configured to apply treatment to the injection site, comprising the steps of: using the fluid injection device, injecting the therapeutic fluid at the injection site; using the treatment element, applying a treatment to at least one of the injection site and adjacent the injection site, wherein the applying of the treatment element causes modification of the temperature of the bodily tissue in a vicinity of the injection site; and improving, based on the applying of the treatment element, a pharmacokinetic and/or pharmacodynamic property of the therapeutic fluid upon application of the treatment.

34. The method according to claim 33, wherein the applying step further comprises applying the treatment at least one of before, during, or after the injecting step.

35. The method according to claim 33, further comprising actuating drug delivery via a trigger.

36. The method according to claim 33, further comprising actuating treatment delivery via a trigger.

37. The method according to claim 33, further comprising selecting a dosage for the therapeutic fluid via a drug dosage selector.

38. The method according to claim 37, wherein the drug dosage selector is configured to apply a bolus dosage of the therapeutic fluid and/or a basal dosage of the therapeutic fluid.

39. The method according to claim 33, further comprising selecting a treatment via a treatment selector.

40. The method according to claim 39, wherein the treatment comprises applying a treatment substance to at least one of the injection site and adjacent the injection site.

41. The method according to claim 40, wherein the treatment substance is selected from a group consisting of: a liquid, ointment, solution, aerosol, foam, solid, gel foam, pressurized liquid, gas, spray, pain reliever drug, analgesic, vasodilatation drug, septic, alcohol, and any combination thereof.

42. The method according to claim 41, wherein the selected treatment is selected from the group consisting of: radiation, light, heat, mechanical vibrations, suction, massaging, acoustic stimulation, electrical stimulation, injection of additional substance(s), and any combination thereof.

43. The method according to claim 33, wherein the therapeutic fluid is insulin.

44. The method according to claim 33, further comprising applying the treatment to at least one of the injection site and adjacent the injection site at least one before, during and after with the injection of the therapeutic fluid.

45. The method according to claim 33, further comprising controlling application of the treatment via a processing unit.

46. The method according to claim 45, further comprising controlling at least one of an amplitude, duration, phase, intensity, and frequency of the treatment via the processing unit.

* * * * *